(12) United States Patent
Kim

(10) Patent No.: US 11,793,962 B2
(45) Date of Patent: Oct. 24, 2023

(54) INTUBATION SYSTEM, METHOD, AND DEVICE

(71) Applicant: Chong S. Kim, Holmdel, NJ (US)

(72) Inventor: Chong S. Kim, Holmdel, NJ (US)

( * ) Notice: Subject to any disclaimer, the term of this patent is extended or adjusted under 35 U.S.C. 154(b) by 408 days.

(21) Appl. No.: 17/110,268

(22) Filed: Dec. 2, 2020

(65) Prior Publication Data

US 2022/0168530 A1 Jun. 2, 2022

(51) Int. Cl.
| | |
|---|---|
| *A61M 16/04* | (2006.01) |
| *A61M 16/00* | (2006.01) |
| *A61B 1/00* | (2006.01) |
| *A61B 1/005* | (2006.01) |
| *A61B 1/267* | (2006.01) |

(52) U.S. Cl.
CPC .... *A61M 16/0488* (2013.01); *A61M 16/0003* (2014.02); *A61M 16/0418* (2014.02); *A61M 2205/583* (2013.01)

(58) Field of Classification Search
CPC .......... A61M 16/0488; A61M 16/0418; A61M 16/0434; A61M 16/0445; A61M 16/0463; A61M 16/0497; A61M 16/0447; A61M 16/0461–0486; A61M 16/0409; A61M 16/0472; A61M 16/0495; A61B 1/00082; A61B 1/0008; A61B 1/00089
See application file for complete search history.

(56) References Cited

U.S. PATENT DOCUMENTS

| | | | |
|---|---|---|---|
| 5,203,320 A | 4/1993 | Augustine | |
| 9,974,912 B2 | 5/2018 | Brain | |
| 11,147,634 B1* | 10/2021 | Nekhendzy | A61B 34/20 |
| 2003/0062039 A1 | 4/2003 | Sniadach | |
| 2003/0225432 A1 | 12/2003 | Baptiste et al. | |
| 2007/0106121 A1 | 5/2007 | Yokota et al. | |
| 2009/0192350 A1 | 7/2009 | Mejia | |
| 2013/0237763 A1 | 9/2013 | Qiu | |
| 2020/0276417 A1* | 9/2020 | Rentschler | A61M 25/0668 |
| 2022/0047832 A1* | 2/2022 | Vaidyanathan | A61M 16/0436 |
| 2022/0362499 A1* | 11/2022 | Mazza | A61M 16/047 |

FOREIGN PATENT DOCUMENTS

| | | |
|---|---|---|
| WO | WO2016147107 A1 | 9/2016 |
| WO | 2018112057 A1 | 6/2018 |

* cited by examiner

*Primary Examiner* — Kendra D Carter
*Assistant Examiner* — Mautin I Ashimiu
(74) *Attorney, Agent, or Firm* — Beau Horner

(57) ABSTRACT

An intubation device utilizes a steerable endotracheal tube guide to position an endotracheal tube at a laryngeal opening, and is also configured for soft tissue retraction to improve visualization of the laryngeal opening. An ETT is positioned within an overtube of intubation device having proximal and distal ends and a flexible tip. The distal end houses a feeder mechanism for displacing the endotracheal tube through the overtube. A hood includes a stem, base, and expandable body and is affixed to the overtube's distal end. The ETT-containing overtube is precisely positioned at a laryngeal opening via positioning effects of body expansion, activation of a tip director, and/or flexible tip articulation. Unhindered visualization of the laryngeal opening is achieved by expansion of the expandable body, pushing soft tissue outwardly and extensibly. An actuation module controls the feeder mechanism as well as the flexible tip to position flexible tip and endotracheal tube.

19 Claims, 18 Drawing Sheets

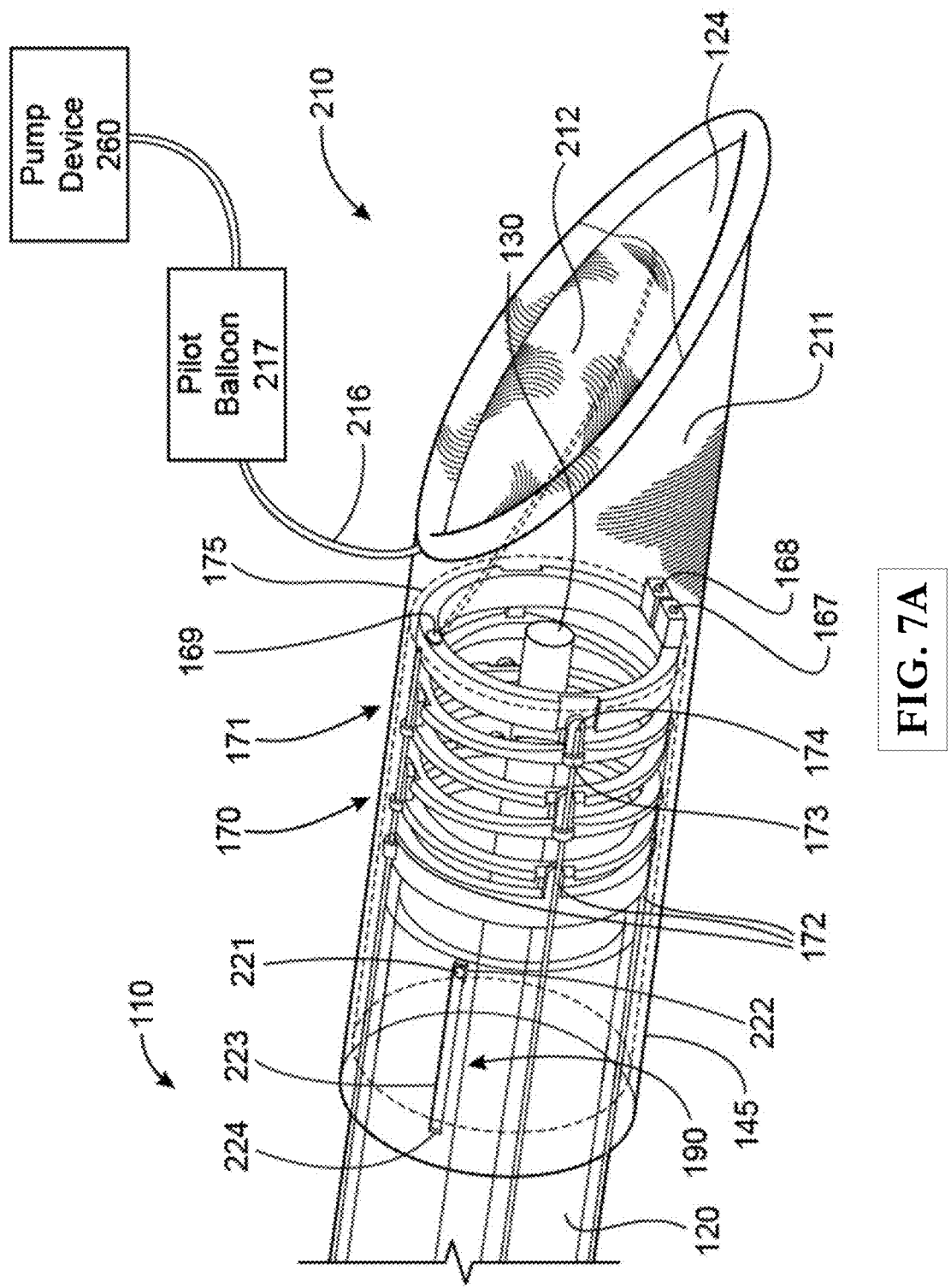

INTUBATION SYSTEM, METHOD, AND DEVICE

CROSS-REFERENCE TO RELATED APPLICATIONS

N/A

FIELD OF THE INVENTION

This invention relates generally to intubation systems, and more specifically to intubation tube insertion devices that provide a clear, unobstructed pathway to a patient's laryngeal opening.

BACKGROUND OF THE INVENTION

The most effective and basic way of securing definitive airway management remains direct laryngoscopy with subsequent placement of an intubation tube.

The laryngoscope consists of a handle and a blade. The blade of a laryngoscope is typically comprised of a flat element usually made of stainless steel and is designed to be placed either in the vallecula (behind the tongue) or posterior to the epiglottis. By lifting up the laryngoscope, then, the mandible, tongue, epiglottis, hyoid bone, and other soft tissue are displaced out of the line of sight of the laryngoscopist in order to expose the glottic opening.

The success of intubation depends on being able to clearly expose the laryngeal opening. Generally accepted ways to improve a limited laryngeal opening are increased elevation of the patient's head and placing the patient in a sniff position which involves extending the atlanto-occipital joint and flexing the lower cervical spine. In cases where cervical immobilization is necessary (e.g., trauma involving possible cervical spine injury), head elevation and cervical spine manipulation are not permitted.

While the majority of cases of intubations are straightforward and simple, difficulty in airways do occur and can result in catastrophic outcomes such as death, brain damage, cardiopulmonary arrest, tracheotomy, and trauma to the pharynx, larynx, and trachea.

There are many causes of difficult intubation: a small mouth, recessed mandible, prominent upper teeth, limited upper cervical spine or atlanto-occipital mobility, limited jaw opening, enlarged tongue, tumors (in the mouth, tongue, larynx, and/or pharynx), obesity with redundant soft tissue, and edema (of the epiglottis, larynx, and/or pharynx).

Tracheal intubation involves placing a flexible plastic tube into the trachea as a conduit to supply oxygen to and eliminate carbon dioxide from a patient. Tracheal intubation is frequently performed for patients who are critically injured, ill, or that require anesthesia. Optimal visualization of the laryngeal opening is best achieved by extending the head and flexing the neck, which is known as a "sniffing position".

Successful intubation requires two distinct processes: clear visualization and identification of the vocal cords and proper insertion of an intubation tube into the trachea. These two processes are equally important. Achieving the first step is of great importance because when the patient is placed under general anesthesia and given paralytic agents, all of the laryngopharyngeal structures become flaccid and collapse, resulting in complete blockage of the airway. During intubation, the operator has to first "clear" the blockage before inserting an ETT. The performance of the second step can be demanding and requires skill and experience. If the former step fails, we have a situation called "can't see and can't intubate." If the latter process fails, we have a situation called "can see but can't intubate."

Proper visualization and identification of the vocal cords is commonly aided by a rigid laryngoscope (which consists of a handle containing batteries that power the light and a rigid and flat blade which is either straight or curved) that is the primary equipment to aid intubation. During intubation, the laryngoscope blade is inserted through the mouth of the patient and positioned in the vallecula (the area between the base of the tongue and the epiglottis; an oval shaped structure located on top of the larynx) and acts as a lid over the laryngeal vestibule that opens into the larynx to prevent the passage of food into the trachea during eating. Once properly placed, the laryngoscope is then pulled anteriorly in an effort to displace the tongue and epiglottis in the upward direction to permit direct visualization of the laryngeal opening.

While its usefulness is unquestioned, rigid laryngoscopes, nonetheless, are not without shortcomings. By virtue of the laryngoscope blades being made of hard metal, traumatic injury to dental structures and soft tissues in the oral cavity and the pharynx are not uncommon. In order to mitigate intubation-related injuries, there exists a need for an approach or a device that can supplant rigid laryngoscopes without compromising results.

As alluded earlier, one of the main functions of rigid laryngoscopes is the displacement of the tongue and the epiglottis from the operator's line of vision. Whilst laryngoscopes are adequate in certain cases, not infrequently, however, they fail simply because they can expose the airway only to the level of the epiglottis and not beyond. Should narrowing, swelling, or excessive soft tissue exist below the level of the epiglottis, the usefulness of rigid laryngoscopes is severely limited. Likewise, its utility is restricted in the presence of factors such as, large tongue, a large tumor in the oral cavity and oropharynx, edematous tongue, receded chin, immobile jaw, elongated upper incisors, stiff and immobile necks, and facial and neck trauma.

In this regard, the development of video laryngoscopes has made an enormous contribution in the betterment of the operator's visualization of the larynx. Video laryngoscopes are distinguished from the traditional laryngoscopes by having a camera and the light installed at the tip of the blade. The presence of the camera at the tip allows the user to inspect the anatomy from the vintage point of the blade tip. It is analogous to having an eye at the tip of the blade.

Notwithstanding these obvious advantages, challenges still remain because the blade of video laryngoscopes is ordinarily positioned at the vallecula (the point between the base of the tongue and the epiglottis). In situations where blockage is present beyond the laryngeal blade, i.e. between the tongue base and the vocal cords, video laryngoscopes are inadequate and cannot better the visualization of the laryngeal opening.

Currently, there exists no solution that proffer methods and/or means that can help to surmount the challenges of exposing the vocal cord when obstructive pathology (such as excessive soft tissue, tumor, infection, edema, and hematoma) exists between the epiglottis and the larynx.

One skilled in art would recognize that the path an ETT takes, rather than being straight, is very much convoluted. In understanding the convoluted pathway an ETT traverses, it is helpful to divide the pathway into three segments: the first segment (from the mouth opening to the posterior pharynx), the second segment (from the pharynx to the base of the epiglottis), and the third segment (from the base of the epiglottis to the trachea through the larynx). Two approximately 90-degree bends exist, the first being between the first and second segments, and the second between the second and third segments. The overall trajectory of an ETT, then, is shaped like an S with two sharp turns.

Recognizing the complex nature of the ETT path, the operator, before intubating, may manually shape the intubation tube by means of a rigid malleable stylet, which is placed inside the ETT. Commonly, the stylet is bent approximately 90 degrees at the junction between the middle and distal one third. The fashioned ETT now has a built-in first pivot, facilitating the operator to advance the ETT through the first and second segments. If problems arising in this phase of intubation can be managed with relative ease, the next phase of intubation (navigating the ETT through the second pivot point) can be more daunting.

An important issue with intubation that cannot be ignored is the need to quickly intubate the patient. There are countless situations where seconds of oxygen deprivation matter to the well-being of the patient. In the cases of difficult airways, it is not uncommon for the operator to take a significant amount of time to intubate. Because the oxygen is held during the intubation process, the patient may suffer from hypoxia.

Another vital aspect of intubation is the existence of technical limitations that force the operator to stop oxygenation during intubation. The most important factors include: presence of a stylet inside the full length of the ETT, inability to control oxygen escaping out of the mouth, and ineffectual means of preventing the air diverted into the stomach. For these reasons, supplying oxygen ceases during the entire duration of intubation. When the patient's blood oxygen level drops to a significant level, the intubation process has to stop immediately. The next intubation attempt can commence only when the patient's oxygen level is raised to a satisfactory level. A repeated stop and go cycle can be frustrating and can reduce the likelihood of successful intubation, not to mention the potential adverse impact on the patient.

BRIEF SUMMARY OF THE INVENTION

The disclosed subject matter provides a system, method, and device utilized to position an ETT (endotracheal tube) into a laryngeal opening of a patient. The device comprises an overtube having a semirigid proximal portion, a flexible distal tip, and a hood. The semirigid portion includes a proximal end and a distal end. The flexible tip affixes to the distal end of the semirigid portion. The distal end may house a feeder mechanism for displacing the ETT. A hood slideably attached to the distal end of the overtube includes a stem, a base, an esophageal seal, and an expandable body. Expansion of the hood bladder may advance the overtube and place the flexible tip in an optimal location (i.e. at the laryngeal opening) with the ETT in alignment with the tracheal axis. An actuation module actuates the wire-controlled flexible tip of the overtube in order to fine-tune the positioning of the flexible tip for arrival at its ultimate position. The ETT may be advanced into the trachea by a plurality of means.

In embodiments, the feeder mechanism may include a first roller and a second roller. The first roller may be laterally displaced by the actuation module towards the second roller in order to retain the ETT. Actuation module may control at least one of a screw mechanism and a spring mechanism that displaces the first roller. Once displaced, at least one of the first and second rollers may be actuated by the actuation module in order to feed the ETT through the flexible tip.

Actuation module, in other embodiments, may control a plurality of wires affixed to the flexible tip of the overtube. The wires may be extended and retracted by actuation module in order to articulate the flexible tip of the overtube. Flexible tip may articulate at least 30 degrees in at least one of a vertical direction and a horizontal direction in response to the extension and retraction of the plurality of wires.

A method is provided for positioning an ETT adjacent a patient's laryngeal opening and inserting an ETT into a patient's trachea. The method includes inserting the device, with an ETT positioned within an overtube, into a patient's throat. The attachment between the hood and the overtube may be unlocked, allowing the overtube to slide/advance within the hood. The hood bladder is inflated via the airtube. Since the anteroinferior portion of the hood body and the distal portion of the overtube are connected, the expandable hood body pulls the overtube anteroinferiorly. An alternative directional wire originating from the anteroinferior portion of the hood body affixed to the distal end of the overtube, when triggered, pulls the overtube adjacent the laryngeal opening. The end result of this positioning motion is the placement of the overtube and the ETT at the opening of the larynx. Thusly positioned overtube may be further adjusted via articulating functionality of the flexible portion of the overtube. The ETT may be advanced into the trachea through a plurality of means.

A method is provided for clearing the soft tissue from the larynx and hypopharynx. The method utilizes an expandable hood body. The body is expanded and becomes rigid and expands in a centrifugal manner. As this occurs, soft tissue is pushed away from the line of vision of the device/user of the device.

BRIEF DESCRIPTION OF THE DRAWINGS

The novel features believed characteristic of the disclosed subject matter will be set forth in any claims that are filed. The disclosed subject matter itself, however, further objectives, and advantages thereof, will best be understood by reference to the following detailed description of an illustrative embodiment when read in conjunction with the accompanying drawings, wherein:

FIG. 7A displays a partial cutaway view of a hood body in a collapsed configuration in accordance with embodiments.

DETAILED DESCRIPTION OF ILLUSTRATIVE EMBODIMENTS

Reference now should be made to the drawings, in which the same reference numbers are used throughout the different figures to designate the same components.

It will be understood that, although the terms first, second, third, etc. may be used herein to describe various elements, these elements should not be limited by these terms. These terms are only used to distinguish one element from another element. Thus, a first element discussed below could be termed a second element without departing from the teachings of the present disclosure.

The terminology used herein is for the purpose of describing particular embodiments only and is not intended to be limiting. As used herein, the singular forms "a", "an", and "the" are intended to include the plural forms as well, unless the context clearly indicates otherwise. It will be further understood that the terms "comprises" and/or "comprising" or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Figure 1:
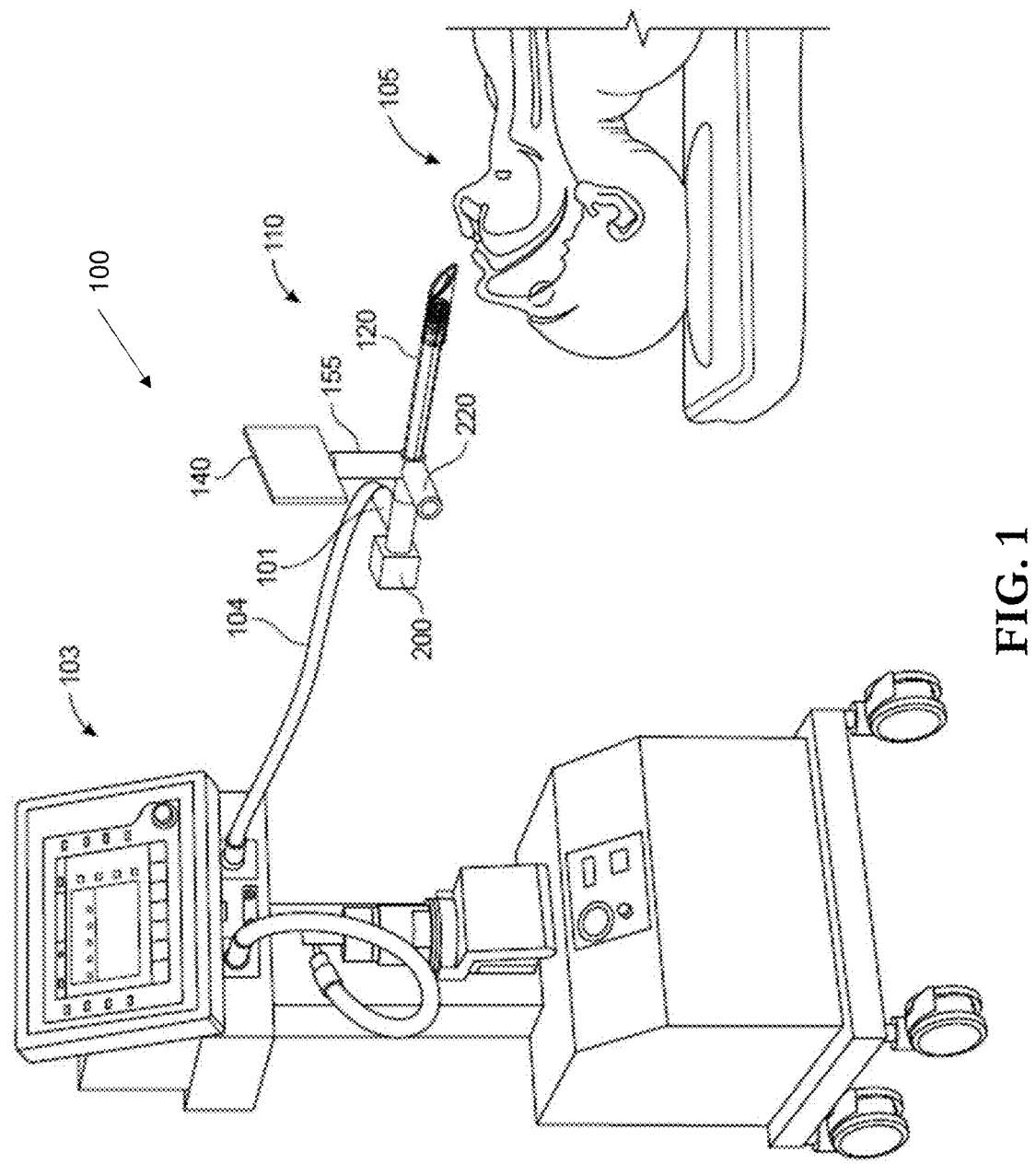
FIG. 1 displays a perspective view of an intubation system in accordance with embodiments.

FIG. 1 displays a perspective view of an intubation system 100 in accordance with embodiments. Intubation system 100 may be utilized to efficiently insert an ETT (endotracheal tube) 130 into a patient's trachea (see FIGS. 7A, 7B, and 7C). System 100 may comprise a ventilator 103, ventilator tubing 104, a ventilator connector 101, and an intubation device 110. Ventilator 103 may be utilized in conjunction with intubation device 110 in order to supply air to a patient 105 while intubation device 110 is being placed within patient 105. Ventilator 103 may, in embodiments, be any type of standard ventilator found in a hospital. Ventilator 103 may include a ventilator tubing 104 that is connectable to a port (not depicted) of ventilator connector 101 (shown in FIG. 1 as a T-joint). Ventilator connector 101 may be hollow in order to allow air to pass through to intubation device 110. In embodiments, ventilator connector 101 may be incorporated as a single body with intubation device 110.

In other embodiments, ventilator connector 101 may affix to intubation device 110 via means including, but not limited to threading, twist-lock engagement, O-ring attachment, magnetic attachment, form-fitting, and male-female engagement. When intubation device 110 is not in use, ventilator connector 101 may be removed for storage purposes. In other instances, ventilator connector 101 may be left on intubation device 110 and a lid 102 may be affixed to an end of intubation device 110 proximal the location of attachment of ventilator connector 101 (see FIG. 2). In embodiments, lid 102 may be affixed to an end of intubation device 110 via means previously mentioned including, but not limited to threading, twist-lock engagement, O-ring attachment, magnetic attachment, form-fitting, and male-female engagement.

Figure 2:
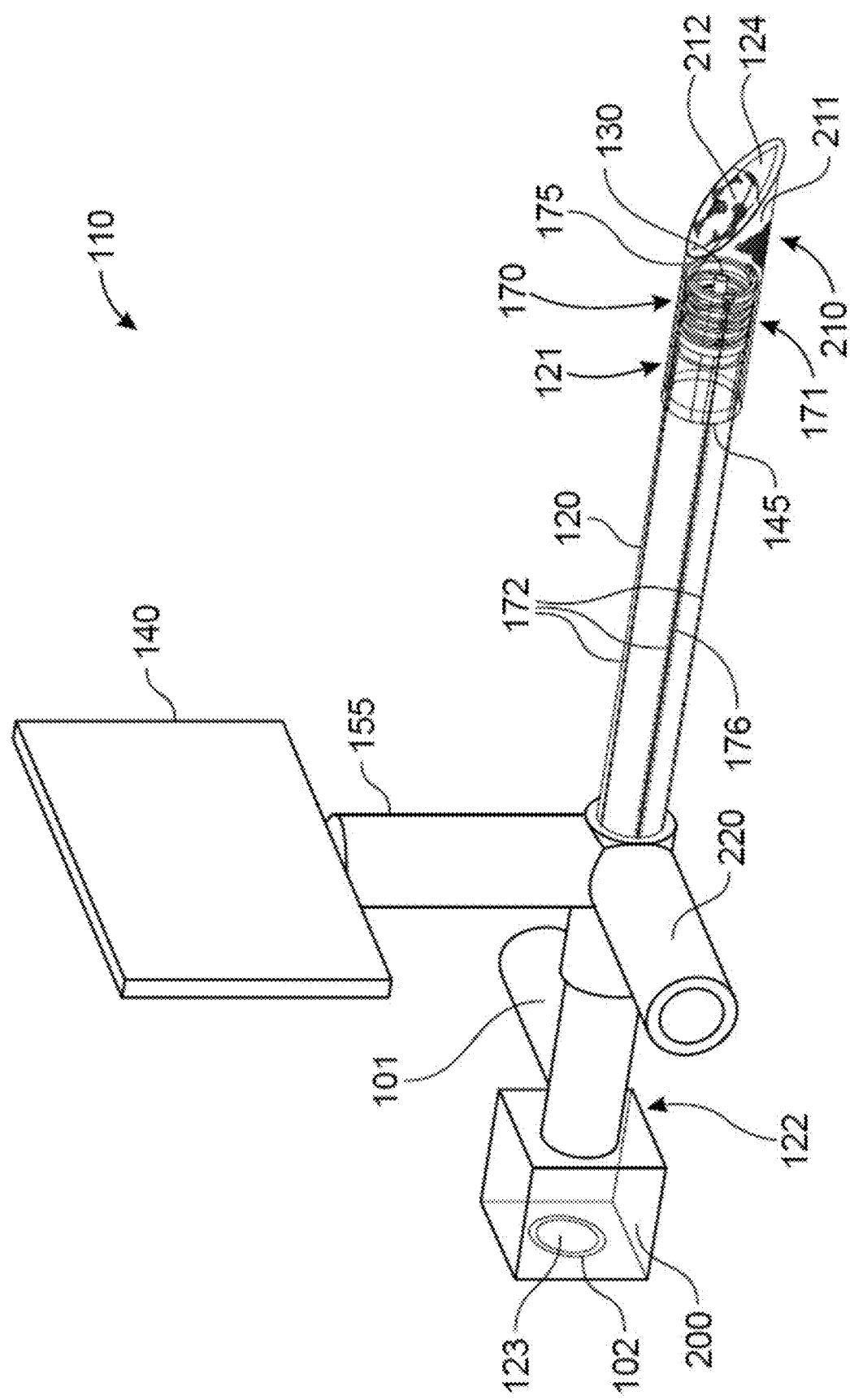
FIG. 2 displays a perspective view of an intubation device in accordance with embodiments.

As shown in FIGS. 1 and 2, ventilator tubing 104 is connected to the open end of ventilator connector 101. One end of the horizontal member of the ventilator connector 101 may be connected to the proximal end 122 of a semirigid portion of overtube 120. The other end of the horizontal member may be affixed to actuation module 200. Intubation device 110 may comprise, in embodiments, a video monitor 140 and a monitor attachment section 155 affixed to overtube 120. These elements may be further described in association with subsequent figures. Handle 220 may be removably affixed adjacent the proximal end 122 of overtube 120. In embodiments, handle 220 may be affixed directly to at least one of monitor attachment section 155 and overtube 120.

In embodiments, ETT (endotracheal tube) 130 may be any other form of medical airway tube. Endotracheal tube (ETT) may also be referred to as an "airway tube" or an "intubation tube".

Figure 3:
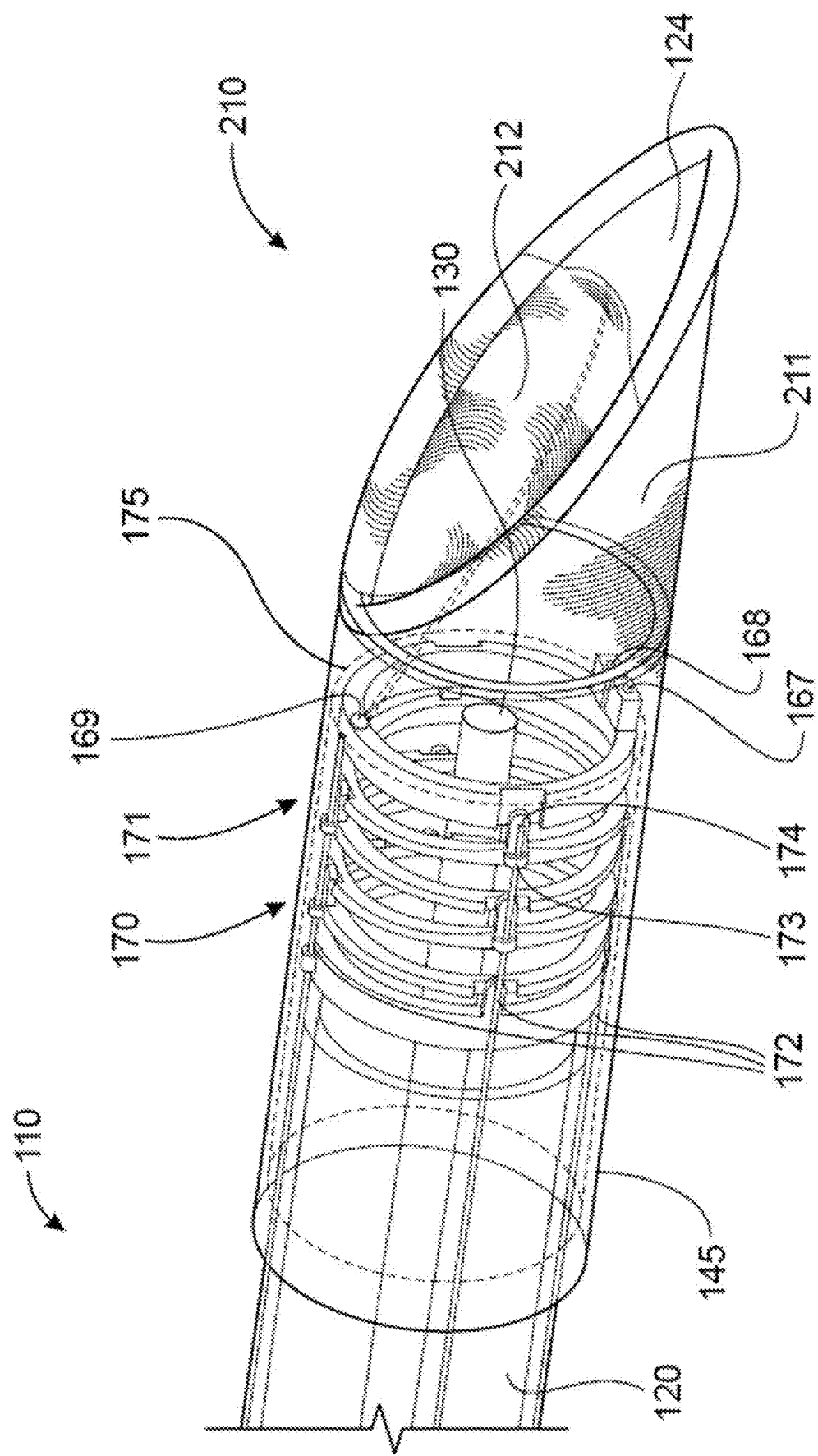
FIG. 3 displays a perspective front view of an intubation device in accordance with embodiments.

FIG. 2 displays a perspective view of an intubation device 110 in accordance with embodiments. Intubation device 110 may be utilized to position an ETT 130 into a laryngeal opening 213 of patient 105. Intubation device 110 may comprise an overtube 120, a flexible tip 170, a stem 145, a hood 210, a video monitor 140, a monitor attachment section 155, a ventilator connector 101, and an actuation module 200. Overtube 120 includes a semirigid proximal portion, a flexible distal tip 170, and a hood 210. Hood 210 may include stem 145, hood base 211 contiguous with a posterior wall of stem 145, esophageal seal (not depicted), and hood body 212 having an expandable structure. The semirigid portion includes a proximal end 122 and a distal end 121. The flexible tip 170 affixes to the distal end 121 of the semirigid portion via the plurality of control wires 172 and malleable covering 175 (depicted in dotted lines in FIG. 3). As shown in FIG. 3, malleable covering 175 may cover the plurality of discs 171 and may be affixed to the distal end 121 of overtube 120. In embodiments, malleable covering 175 may be affixed to the distal end 121 of overtube 120 via at least one of ultrasonic welding, thermal bonding, and adhesive.

Overtube 120 may comprise an interior surface, an exterior surface, and an interior space that may house at least the ETT 130. Semirigid portion of overtube 120 may be designed to be semi-rigid/semi-flexible and may be made from a material in order to meet certain rigidity/flexibility requirements (such as, but not limited to, bending to efficiently fit within a patient's throat 214). In certain embodiments, overtube 120 may comprise polymer tubing such as, but not limited to polyvinyl chloride (PVC), silicone, and/or other thermoplastic materials. In embodiments, portions of the semirigid portion of overtube 120 may comprise a corrugated configuration in order to allow for additional flexibility.

Flexible tip 170 may be disposed within hood 210 and/or stem 145; both the flexible tip 170 and hood 210 may maintain rigidity and attachment to overtube 120 via stem 145. Stem 145 is a tubular portion of hood 210 that may overlap the semirigid portion of overtube 120 and flexible tip 170 so that flexible tip 170 and additional material of hood 210 are secured between stem 145 and exterior surface of overtube 120. In certain embodiments, stem 145 may be removably affixable to overtube 120 using any of the aforementioned affixing means.

Flexible tip 170 may be fashioned to be more flexible than overtube 120 and may be freely contained within at least one of the stem 145 and hood 210. Flexible tip 170 may articulate 30 degrees or more in a vertical and/or horizontal direction within flexible tip 170 so that when device 110 is positioned adjacent a laryngeal opening 213 of a patient 105, flexible tip 170 may be manipulated to aim directly at the laryngeal opening 213 so that an ETT 130 (or other intubation tube) may be easily fed into the laryngeal opening 213 (and not into esophageal opening 215).

Monitor attachment section 155 may be affixed to an exterior surface of overtube 120 so that video monitor 140 may be maintained in a position viewable by an individual using device 110 when device 110 is positioned within the throat 214 of a patient 105. In certain embodiments, monitor attachment section 155 may be removably affixable so that the position of monitor attachment section 155 and video monitor 140 may be adjusted.

To insert the ETT 130 into device 110, the ETT 130 may be manually advanced through either the proximal opening (actuation module orifice 123) or distal opening 124 of hood 210 until the ETT 130 is positioned completely inside overtube 120. In embodiments, internal components of device 110 may hold ETT 130, at least temporarily, in place within device 110.

The plurality of control wires 172 affixed to the flexible tip 170 may be utilized to manipulate the position of the flexible tip 170. The plurality of control wires 172 may be connected to an actuation module 200 positioned at proximal end 122 of overtube 120. Each of the wires 172, in embodiments, may be surrounded by a flexible sheath 176 (see dotted line surrounding middle wire 172) that may be affixed to an interior surface of overtube 120 in order to keep wires 172 isolated from the ETT 130 or other components found within overtube 120. The flexible sheath 176 may also be constructed to flex with overtube 120 when overtube 120 is flexed within a patient 105. Flexible sheath 176 may be made of the same or a similar material as that of overtube 120. In other embodiments, each of the wires 172 may be positioned adjacent an exterior surface of overtube 120. The wires 172 may be surrounded by a flexible sheath 176 that may be affixed to an exterior surface of overtube 120 in order to keep wires 172 isolated from any interior components found within overtube 120. In embodiments, flexible sheath 176 may be affixed to overtube 120 via one or more attachment means such as, but not limited to, adhesive, heat bonding, solvent bonding, and ultrasonic welding.

It is noted that the wires 172 may embody a medium to low flexural rigidity in order for the wires 172 to bend with overtube 120 but may also embody a high compressive force in order for the wires 172 to be pushed forward in the flexible tip 170 so that flexible tip 170 may be moved in one or more directions. In certain embodiments, wires 172 may comprise an elastic material.

FIG. 3 displays a perspective front view of an intubation device 110 in accordance with embodiments. As shown, flexible tip 170 may comprise an interior frame comprising plurality of discs 171 spaced apart from one another as well as a malleable covering 175. Alternatively, flexible tip 170 may be a spring of sufficient flexibility covered with malleable covering 175. The four wires 172 may extend through loops 173 positioned on all discs 171 except for the disc 171 closest to distal opening 124; wires 172 may include wire ends 174 anchored to the disc 171 closest to the distal opening 124. This configuration may allow for the movements of all disks 171 when wires 172 are actuated. As shown, the four wires 172 may be equally spaced around the circumference of overtube 120. The four wires 172 may be separated into pairs of wires 172 (left-right and top-bottom). The left-right pair of wires 172 controls the flexible tip 170 bending left and right, while the top-bottom pair of wires 172 controls the flexible tip 170 bending up and down. Actuation module 200 actuates wire-controlled flexible tip 170 of overtube 120 in order to fine tune the positioning of the flexible tip 170 for arrival at its ultimate position once flexible tip 170 is positioned at the laryngeal opening 213. ETT 130 may be advanced into the trachea by a plurality of means.

In order to keep the discs 171 stationary (not sliding along wires 172) and spaced from one another, a malleable covering 175 may be disposed around the discs 171. The malleable covering 175 may be thin and may comprise a high flexural strength; covering 175 may comprise a polymeric material such as, but not limited to, polytetrafluoroethylene (PTFE), fluorinated ethylenepropylene (FEP), perfluoroalkoxy (PFA), ethylene tetrafluoroethylene (ETFE), polyether ether ketone (PEEK), polyvinyl chloride (PVC), and rubbers. In other embodiments, covering 175 may be corrugated in order to keep discs 171 from sliding along wires 172. In other embodiments, resilient devices, such as, but not limited to springs, may be positioned between and attached to adjacent discs 171 in order to keep discs 171 stationary and allow for flexibility when in use.

Hood 210 may comprise a base 211, a hood body 212, and an inferior projection acting as an esophageal seal (not depicted). Base 211 may comprise a solid semi-flexible structure and may be designed to sit against the posterior hypopharyngeal wall. Hood body 212 is affixed to base 211 and may provide the function of applying pressure to the soft tissue in the laryngeal vestibule and the hypopharynx of an individual so as to retract the soft tissue out of the line of vision of the device 110/a user of intubation device 110. Hood body 212 may be fashioned as a dome-shaped expandable/inflatable structure affixed to the sides of base 211. In embodiments, hood body 212 may be half frusto-spherical or half frusto-conical in shape (roughly frusto-spherical or frusto-conical in shape in combination with base 211. The superior portion of the body 212 (adjacent overtube 120) may be contiguous or non-contiguous with the superior portion of body 212. The inferior portion, which faces the larynx when in use, is left open. In certain embodiments, hood body 212 may comprise an expandable/inflatable section having an inflating bladder made of soft plastics and/or fabrics. A deflated/collapsed hood body 212 may be inflated to a rigid/expanded state and may inflate outwardly away from base 211 to push out the soft tissue from the hypopharynx and laryngeal vestibule 213. Additionally, hood body 212 may be made taut and may be advanced anteriorly by a plurality of mechanisms including at least one of a hydraulic, pneumatic, and electromechanical system in order to apply pressure anteriorly to the hood body 212 to push out the soft tissue from the hypopharynx and laryngeal vestibule 213 (hood body 212 may act as a tent and may, in embodiments, include an expandable frame/element and/or expandable covering). The esophageal seal (not depicted) may be an inferior projection of hood body 212 and may comprise a solid, semi-flexible structure. It may serve to occlude the esophageal opening 215 when device 110 is positioned properly within a throat 214. In embodiments, esophageal seal may be any type or configuration of esophageal seal found in the art. Once device 110 is placed in the throat 214, deflated inflatable bladder of hood body 212 is inflated to a rigid state and inflates outwardly away from base 211 to push out the soft tissue from the hypopharynx and laryngeal vestibule 213. After the soft tissue is cleared out of the field of vision of a user of device 110, overtube 120 is advanced via a plurality of mechanisms including, but not limited to, an attachment means (tip director 169/ alternative tip director 165) between the hood body 212 and flexible tip 170 of overtube 120 or base 211 and flexible tip 170. In embodiments, stem 145 and base 211 may be one contiguous part (made of the same material). It is noted that hood body 212 may be described as being in a retracted state when hood body 212 is not expanded and in an expanded state when hood body 212 is inflated/expanded to a rigid structure.

Via the tip director 169, the two processes of the soft tissue clearing and the overtube 120 positioning are effected simultaneously when hood body 212 is expanded.

When flexible tip 170 is positioned (by the inflating action of inflatable bladder/expansion of hood body 212) adjacent a laryngeal opening 213 of a patient 105, flexible tip 170 may be further maneuvered to precisely align overtube 120 with the laryngeal opening 213 of a patient 105 via manipulation of wires 172 using the mechanisms found in actuation module 200. Tip director 169 and its functionality may be discussed further in the following paragraphs.

Mechanisms in actuation module 200 may administer applied forces to one or more of the wires 172 so that wires 172 may be extended and/or retracted in flexible tip 170, which may adjust the position of flexible tip 170. In embodiments, the mechanisms may include one or more motors 250 (see FIG. 8) that control one or more wind-up/retraction systems (not shown) that may administer an applied force to the wires 172, which may pull or push the wires 172 (thus moving flexible tip 170). In other embodiments, the mechanisms may include ends of a pair of wires 172 affixed to a first chain 188 (see FIG. 8). First chain 188 may be rotated by one or more gears 255 actuated by one or more motors 250. The other two ends of the remaining pair of wires 172 may also be affixed to a second chain 198 that may be rotated by one or more gears 255 actuated by one or more motors 250. The rotation of the gears 255 may administer an applied force to the wires 172, which may pull or retract one wire 172 in a pair and push or extend the other wire 172 in the pair (thus moving flexible tip 170). In embodiments, each of the gears 255 may be actuated by separate motors 250 or both may be actuated by a single motor 250. Each of the described mechanisms may be positioned within actuation module 200 for proper functionality within device 110. It is noted that one skilled in the art can conceive of and create the components contained in actuation module 200 (such as, but not limited to the one or more motors 250 and the one or more wind-up/retraction systems).

A camera 168 and a light source 167 may be positioned on the distal portion of flexible tip 170. These elements help an individual using device 110 to view the location of flexible tip 170 in relation to the laryngeal opening 213 of a patient 105 (when device 110 is inserted into a throat 214) so that the individual may manipulate the device 110 to an optimal positioning within throat 214 to allow flexible tip 170 to extend into laryngeal opening 213. Wiring of the light source 167 may extend through device 110 to a power source 257 (see FIG. 8) positioned in monitor attachment section 155. Wiring of the camera 168 may also extend through device 110 to power source 257 positioned in monitor attachment section 155. Additional wiring of the camera 168 may extend through device 110 and monitor attachment section 155 to monitor 140 to provide a video feed inside of a patient 105 when device 110 is adjacent a laryngeal opening 213.

The wiring of camera 168 and light source 167, in embodiments, may be surrounded by a flexible sheath (similar to or the same as the flexible sheath 176 covering the wires 172) that may be affixed to either an interior surface of overtube 120 or an exterior surface of overtube 120 depending on whether the wiring is run along an interior surface or an exterior surface of overtube 120. This may allow the wiring to be isolated from other components of device 110. The flexible sheath of the wiring of camera 168 and light source 167 may be constructed to flex with overtube 120 when overtube 120 is flexed within a patient 105. Flexible sheath may be made of the same or a similar material as what overtube 120 is made of. In embodiments, flexible sheath may be affixed to overtube 120 via one or more attachment means such as, but not limited to, adhesive, heat bonding, solvent bonding, and ultrasonic welding.

In other embodiments, flexible tip 170 may include a malleable covering 175 without discs 171. In this configuration, wires 172 may be affixed to a portion of covering 175 closest to distal opening 124 in order to allow for manipulation of flexible tip 170. It is noted that in this embodiment, malleable covering 175 may comprise a polymer that maintains its structural integrity without using discs 171.

In other embodiments, interior frame of flexible tip 170 may comprise a spring as opposed to discs 171. In this configuration, wires 172 may be affixed to a portion of the spring closest to distal opening 124 in order to allow for manipulation of flexible tip 170. It is noted that in this embodiment, the spring may provide a more stable interior frame/user experience due to the compressive force of the spring in combination with the extension and retraction of wires 172.

In other embodiments, actuation module 200, wires 172, flexible sheaths 176, and loops 173 may be absent from device 110. In this configuration of device 110, flexible tip 170 may include either discs 171 and a malleable covering 175 or may only include a malleable covering 175. With the absence of wires 172 and other components used by wires 172, flexible tip 170 may rely on tip director 169 or alternative tip director 165 to position flexible tip 170 adjacent a laryngeal opening 213.

In other embodiments, the setup and number of wires 172 may vary. For example, device 110 may comprise less than four wires 172 or more than four wires 172 positioned similarly or differently than the example described above.

Figure 4:
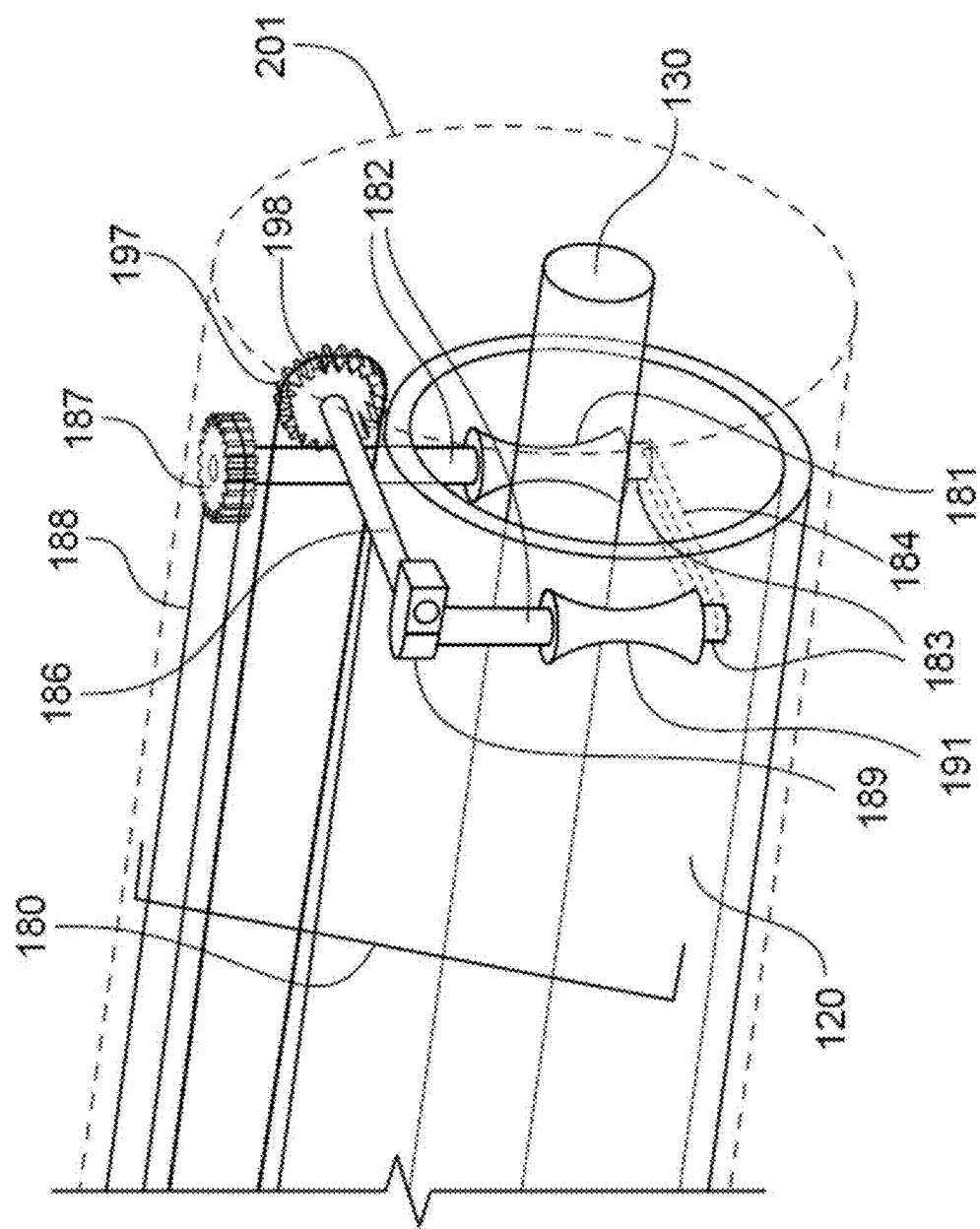
FIG. 4 displays a partial cutaway view of an intubation device having a feeder mechanism in accordance with embodiments.

FIG. 4 displays a partial cutaway view of an intubation device 110 having a feeder mechanism 180 in accordance with embodiments. The feeder mechanism 180 may be positioned at the junction of the flexible tip 170 and semi-rigid portion of the overtube 120 (partially or fully overlapped by stem 145) and may function to advance ETT 130 through overtube 120 and out of the distal end 121 of overtube 120. Feeder mechanism 180 may include a pair of diametrically opposed rollers 181, 191. A first roller 181 may be stationary and may be incorporated into an interior wall of overtube 120 via a base 183. First roller 181 may be affixed to base 183 via a shaft 182, which also juts out of the top side of first roller 181. Base 183 may include a bearing engageable with shaft 182 so that first roller 181 may rotate. To control the spinning movement of first roller 181, shaft 182 at the top side of first roller 181 may be affixed to a first gear 187 positioned horizontally in relation to first roller 181; first gear 187 may be driven by a first chain 188 that extends into actuation module 200 which houses a gear 255 affixed to a motor 250 (see FIG. 8) that turns first gear 187 and causes first chain 188 to move (thus rotating first roller 181).

Second roller 191 may include a shaft 182 that juts out of a top side of second roller 191. The shaft 182 of second roller 191 may be affixed to a screw receiver 189 that juts outward towards the distal end 121 of overtube 120 (in relation to where second roller shaft 182 is affixed to screw receiver 189). In certain embodiments, a screw shaft 186 may be positioned within screw receiver 189 at one end and may be affixed to an interior wall of overtube 120 at a screw shaft base (not depicted) adjacent first roller 181. The screw shaft base may include a bearing in order to allow screw shaft 186 to rotate. This configuration may be constructed on either end of screw shaft 186. In embodiments (as depicted in FIG. 4), when portions of the feeder mechanism 180 are positioned externally to overtube 120, screw shaft base may be affixed to an exterior wall of overtube 120 in this instance. Additionally, it is noted that screw receiver 189 and screw shaft 186 both comprise threads that allow the screw shaft 186 to move/twist through screw receiver 189.

A second gear 197 may be affixed to a second chain 198 that extends into actuation module 200 which houses a gear 255 affixed to a motor 250 that turns second gear 197 and causes second chain 198 to move, thus rotating screw shaft 186 and causing screw receiver 189 and second roller 191 to move laterally towards first roller 181. This in turn forces both the first roller 181 and the second roller 191 to engage ETT 130 and securely feed ETT 130 through distal opening 124 of device 110 (ETT 130 moves due to the rotation of first roller 181). In this instance, ETT 130 is "automatically" fed through distal opening 124. In embodiments, first and second rollers 181,191 may be covered with a material with a high coefficient of friction and may be shaped to conform to the contour of ETT 130.

In other embodiments, a spring may be utilized in place of screw shaft 186. One end of a spring may affix to screw receiver 189, while the other end may affix to either the shaft 182 of first roller 181 or to the interior surface of overtube 120. When ETT 130 is positioned between first roller 181 and second roller 191, the spring may extend to allow second roller 191 to move laterally away from first roller 181 to provide a secure feeder mechanism 180 for ETT 130. In some instances, an inner support shaft may be positioned within the spring (and affixed to screw receiver 189 and either the shaft 182 of first roller 181 or the interior surface of overtube 120) in order to avoid lateral bending of the spring.

Figure 8:
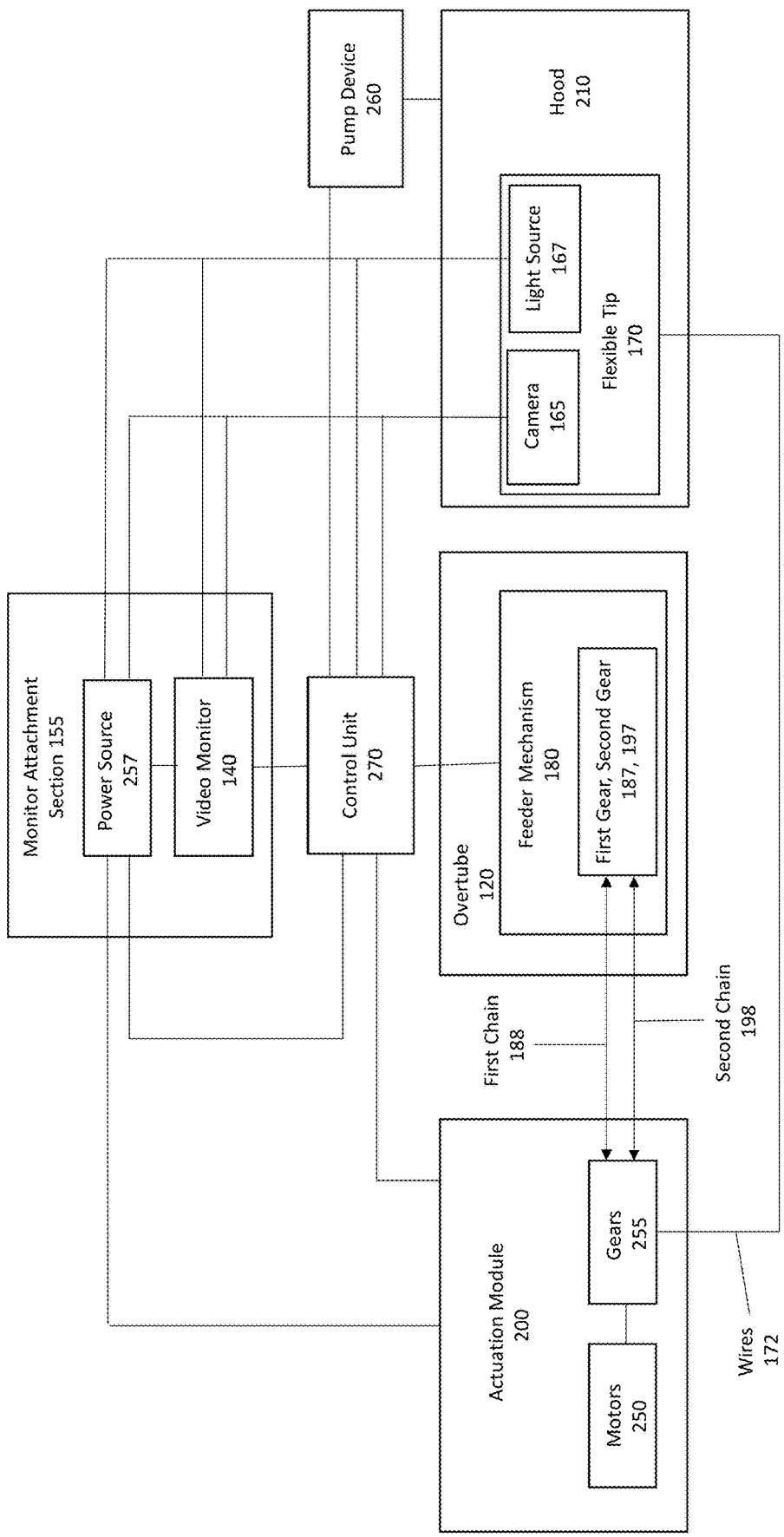
FIG. 8 displays a components diagram of an intubation device in accordance with embodiments.

It is noted that the actuation of feeder mechanism 180 may be carried out either by hand, such as, but not limited to, using one or more hand cranks, or using a control unit 270 (see FIG. 8). Control unit 270 may include a user input for controlling the motors 250 that run the gears 255 and chains 188,198 for controlling feeder mechanism 180.

In any of the aforementioned embodiments, a base 183 of second roller 191 may be disposed within a roller track 184 in order to keep the second roller 191 balanced and avoid shifting within overtube 120. Roller track 184, in embodiments, may comprise walls on each side of second roller base 183 that extend from one side of overtube 120 to the other in order to have second roller 191 avoid shifting problems and keep it moving along a path across the width of overtube 120.

In embodiments, one or more components of feeder mechanism 180 may be disposed outside of overtube 120. These components may be covered by an outer covering 201. For example, first and second gears 187,197 may be positioned outside of overtube 120; outer covering 201 may only cover these components. It is noted that outer covering 201 may be affixed to overtube 120 so that overtube, including outer covering 201, is airtight.

Figure 5:
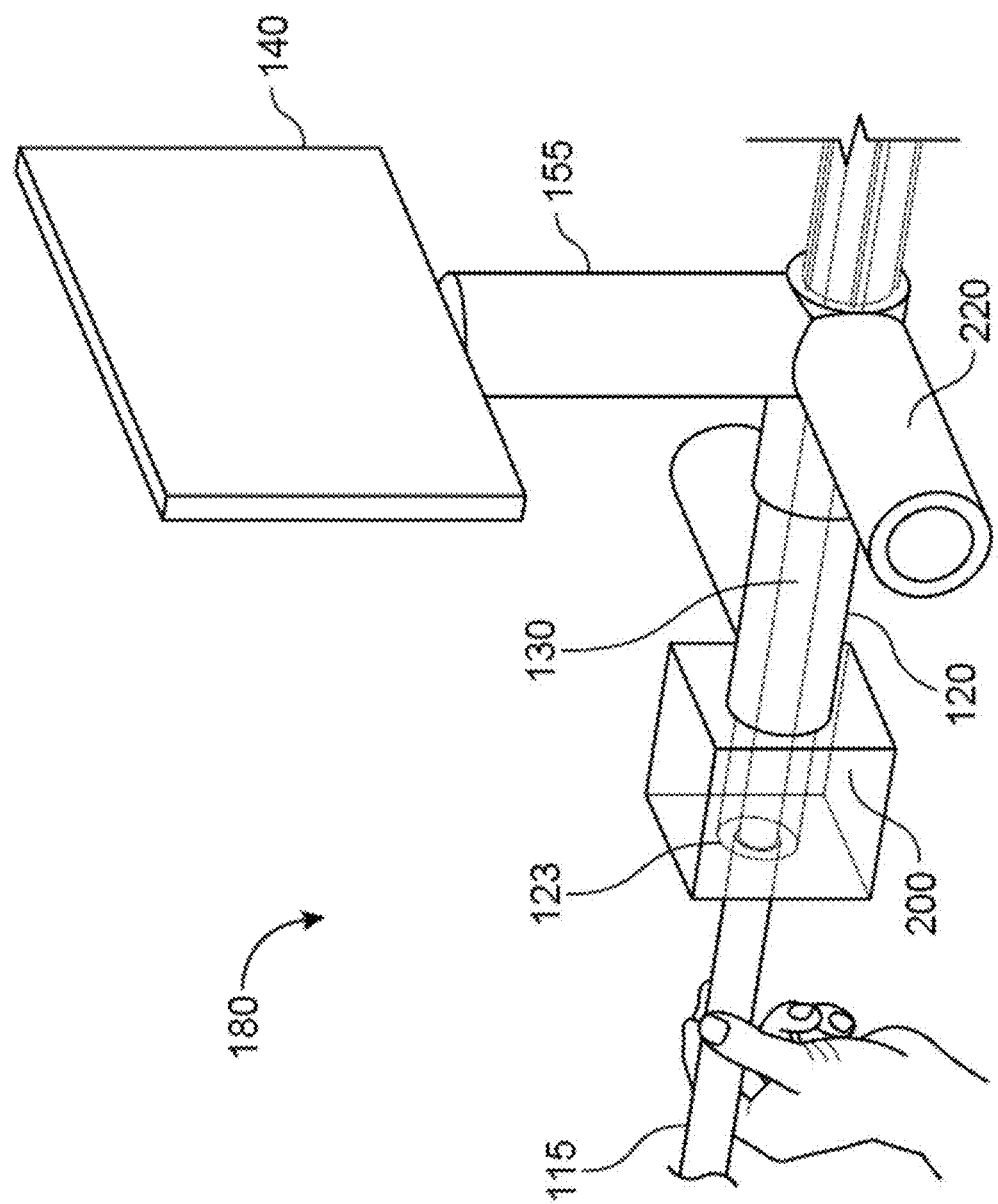
FIG. 5 displays a partial cutaway view of an intubation device having an alternative feeder mechanism in accordance with embodiments.

FIG. 5 displays a partial cutaway view of an intubation device 110 having an alternative feeder mechanism 180 in accordance with embodiments. Feeder mechanism 180 found in FIG. 5 may be an alternative feeder mechanism 180 that may be utilized to advance ETT 130 through overtube 120 and out of the distal opening 124 of hood 210. Lid 102 (see FIG. 2) of actuation module 200 may be taken off to reveal an orifice (actuation module orifice 123) that may extend through actuation module 200 to overtube 120. In order to advance ETT 130, an individual operating device 110 may use a rod 115 to manually push and advance ETT 130 through overtube 120. This may be carried out in order to push ETT 130 into the laryngeal opening 213 of a patient 105 once the flexible tip 170 is positioned adjacent a laryngeal opening 213.

Figure 6:
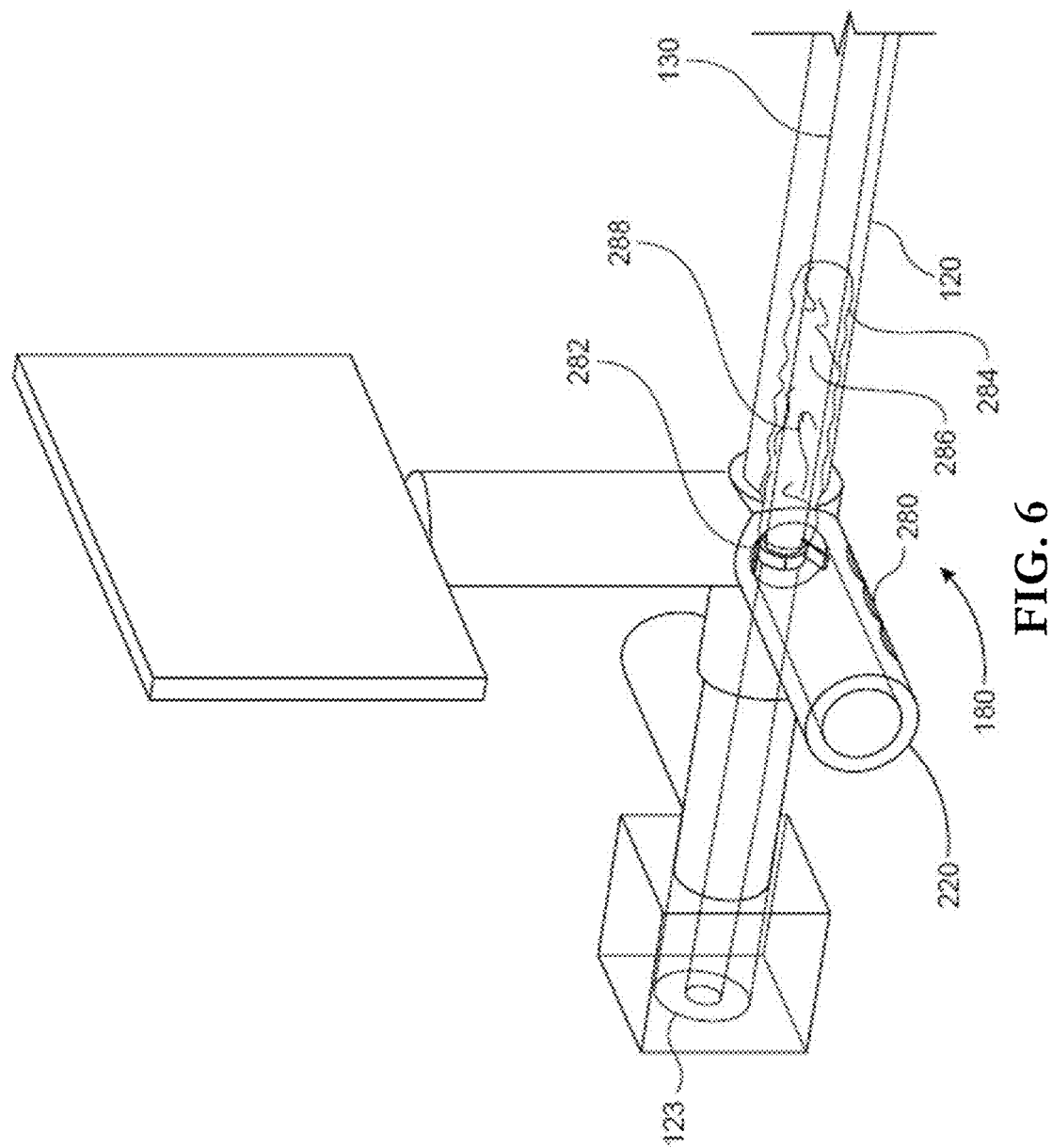
FIG. 6 displays a partial cutaway view of an intubation device having an alternative feeder mechanism in accordance with embodiments.

FIG. 6 displays a partial cutaway view of an intubation device 110 having an alternative feeder mechanism 180 in accordance with embodiments. Feeder mechanism 180 found in FIG. 6 may be an alternative feeder mechanism 180 that may be utilized to advance ETT 130 through overtube 120 and out of the distal opening 124 of hood 210. Handle 220 may include a trigger mechanism 280 that may be actuated by the hand of a user of device 110. Trigger mechanism 280 may be affixed to a clamp 282 so that when trigger mechanism 280 is disengaged, clamp 282 securely clamps onto ETT 130 so that ETT 130 does not shift in any direction/is stationary. When clamp 282 is secured, handle 220 may be shifted along the length of overtube 120 to advance ETT 130 out of the distal opening 124 of hood 210. To keep handle 220 secure and device 110 airtight, handle 220 may be run along a track 286 (such as an extended male-female engagement system/track, etc.) affixed to or within device 110. The area surrounding track 286 (the length of device 110 where handle 220 moves in track 286), referred to as the extension zone 284, may be covered with malleable covering 288 which may comprise a polymeric covering (similar to material surrounding a stick shift in an automobile). Malleable covering 288 may comprise an elasticity to allow a user to move handle 220 laterally and to keep device 110 airtight. It is noted that handle 220 may be able to move ETT 130 a longer or shorter distance depending on the elasticity of malleable covering 288.

It is noted that one skilled in the art can conceive of and create the components for affixing trigger mechanism 280 to clamp 282 so that when trigger mechanism 280 is actuated, clamp 282 securely clamps onto ETT 130.

FIG. 7A displays a partial cutaway view of a hood body 212 in a collapsed configuration in accordance with embodiments. Inflatable bladder of hood body 212 may cover a portion of distal opening 124 when deflated. An upper end of hood body 212 may be affixed to one end of an inflation tube 216 that may run along an exterior surface of overtube 120. The other end of inflation tube 216 may be affixed to a pilot balloon 217 and a pump device 260 (FIG. 8) having a one-way valve that may feed air into inflatable bladder. When it is determined that device 110 is properly positioned within throat 214, an individual may use pump device 260 to inflate inflatable bladder 212 so that it becomes rigid and concave in shape and pushes out the soft tissue from the hypopharynx and laryngeal vestibule 213 in throat 214, providing an airtight enclosure.

Figure 7B:
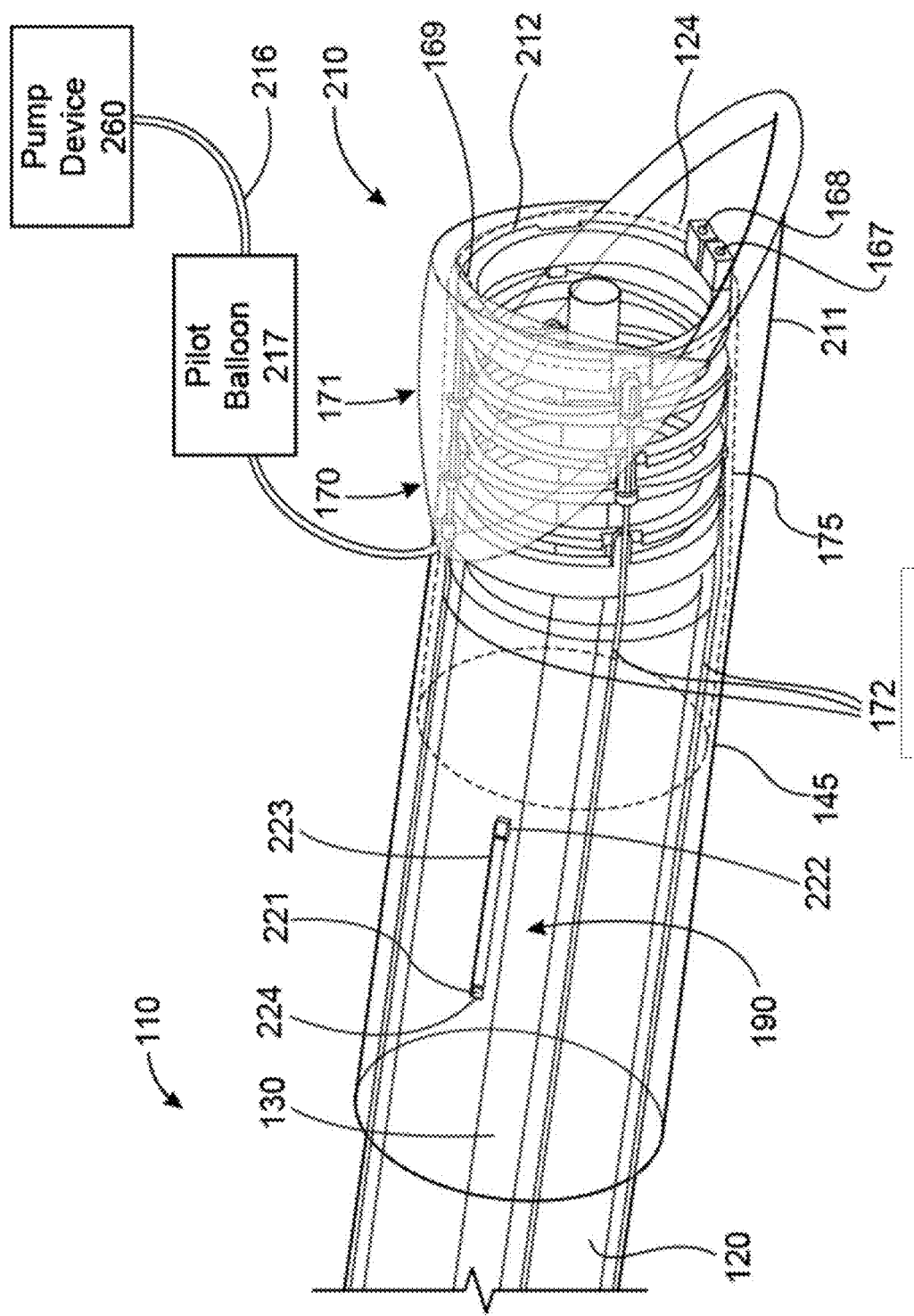
FIG. 7B displays a partial cutaway view of a hood body in an expanded configuration in accordance with embodiments.

As shown in FIG. 7B, when inflatable bladder is inflated/hood body 212 is expanded with tip director 169 being affixed to flexible tip 170 and hood body 212, one or more additional mechanisms may be triggered. In embodiments, tip director 169 may be at least one of a wire, an elastic cord, and an elastic polymer. The inflation of inflatable bladder may clear the soft tissue from the hypopharyngeal and laryngeal vestibule and may also automatically pull flexible tip 170 anteriorly and inferiorly and position flexible tip 170 at the laryngeal opening 213 of patient 105 and increases the likelihood of successful insertion of ETT 130 into the laryngeal opening 213. Flexible tip 170 may be pulled farther (along with overtube 120) in response to locking mechanism 190 being unlocked/in an unlocked position or state and in response to the expansion of hood body 212. In this case, stem 145 may be slidably attached to overtube 120 via the locking mechanism 190. As shown, a protrusion 221 affixed to the interior surface of stem 145 is pulled out of a pocket 222 positioned on the exterior surface of overtube 120 in response to the force exerted by the inflation of inflatable bladder on flexible tip 170 by way of tip director 169. Protrusion 221 is pulled along a path 223 (with a depth shallower than pocket 222) as flexible tip 170 and overtube 120 are pulled by hood body 212 until protrusion 221 hits wall 224 that is positioned at an end of path 223. In embodiments, device 110 may comprise this aforementioned embodiment of locking mechanism 190 in multiple areas around overtube 120 and stem 145. In certain embodiments, protrusion 221 may circumnavigate the interior surface of stem 145, while pocket 222, path 223, and wall 224 may circumnavigate the exterior surface of overtube 120 and may function similarly to the above described locking mechanism 190.

Figure 7C:
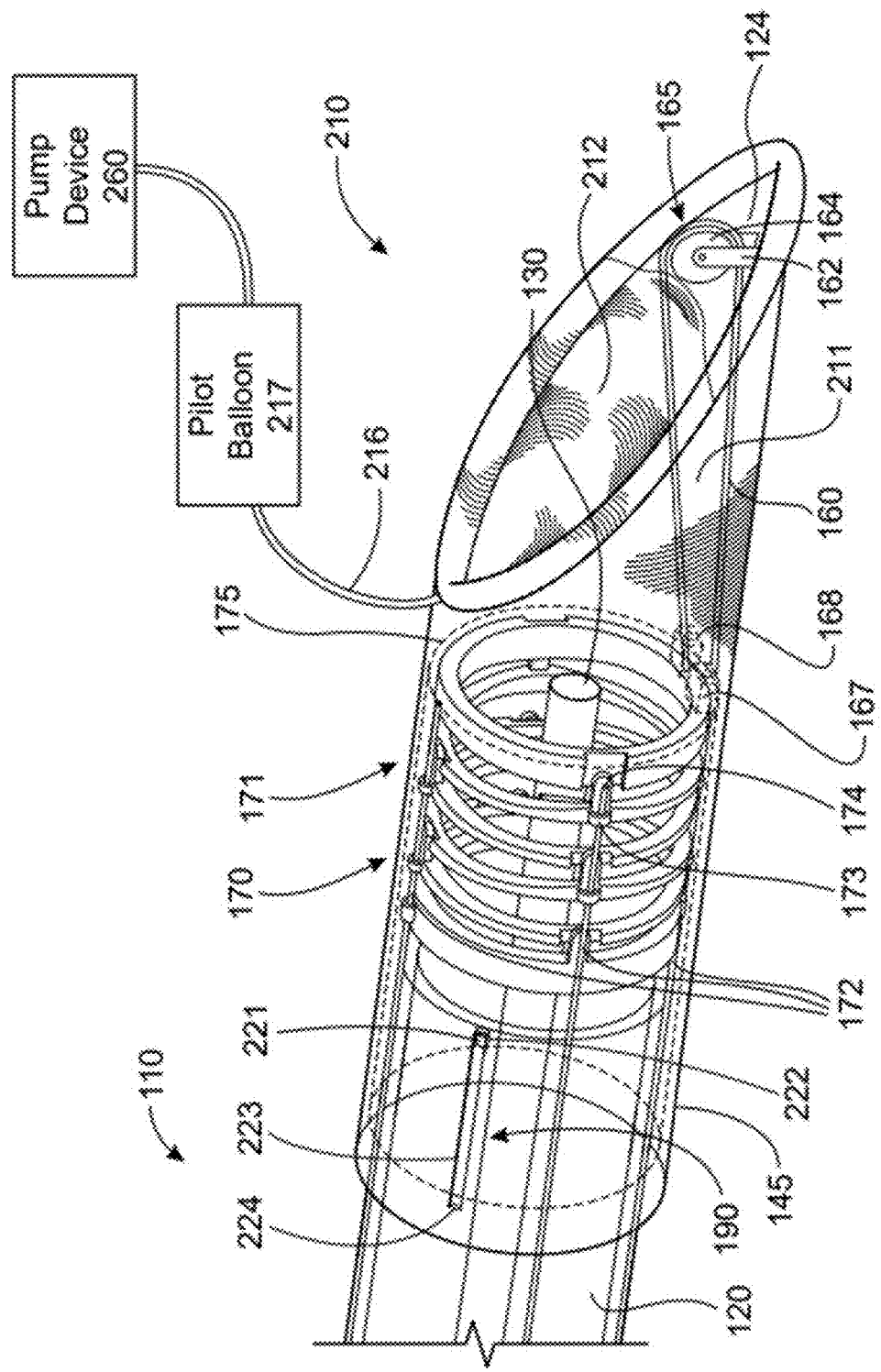
FIG. 7C displays a partial cutaway view of a hood body in a collapsed configuration including an alternative tip director in accordance with embodiments.

FIG. 7C displays a partial cutaway view of a hood body 212 in a collapsed configuration including an alternative tip director 165 in accordance with embodiments. Alternative tip director 165 may include pulley wire 160, pulley base 162, and pulley 164. Pulley wire 160 may, in embodiments, be the bottom wire 172 and may be positioned the same as the bottom wire 172. In other embodiments, pulley wire 160 may be positioned adjacent the bottom wire 172 and may be affixed to loops (similar to 173) or a covering on the exterior surface of overtube 120 or may exist freely of loops or guidance means. Pulley 164 may be affixed to hood base 211 via pulley base 162, which may be affixed to hood base 211 or may be integrated with hood base 211 as a single, integrated piece. It is noted that pulley wire 160 may be positioned along the underside of overtube 120 between overtube 120 and stem 145 so that alternative tip director 165 functions properly. In embodiments, pulley wire 160 may be at least one of a wire, an elastic cord, and an elastic polymer.

Figure 7D:
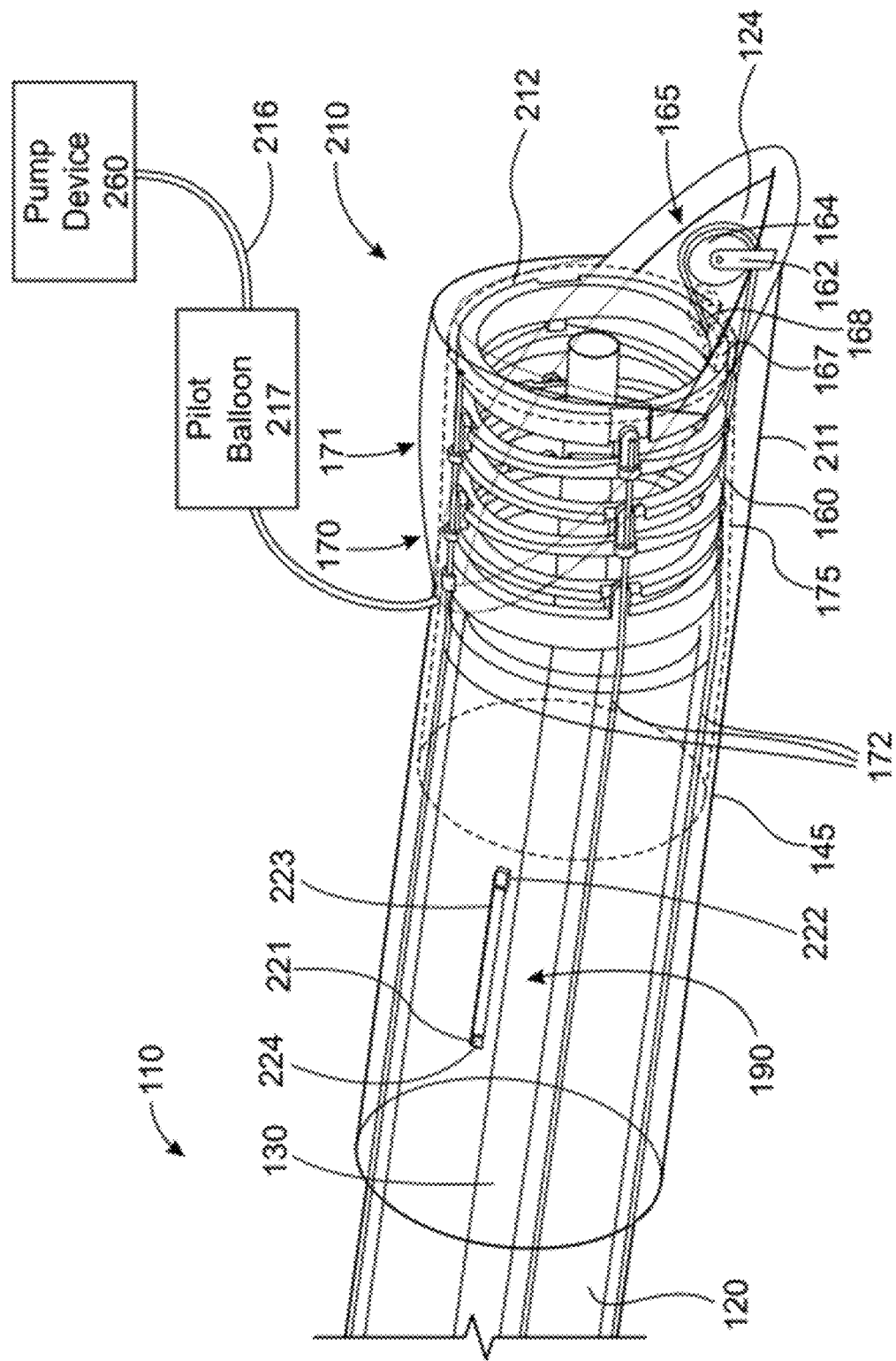
FIG. 7D displays a partial cutaway view of a hood body in an expanded configuration including an alternative tip director in accordance with embodiments.

As shown in FIG. 7D, the pulling forward of the flexible tip 170, in this embodiment, may be separate from the expansion of body 212 (which is what is used to pull flexible tip 170 forward in FIGS. 7A and 7B). In this embodiment, pulley wire 160 may be pulled toward the rear of overtube 120 via automatic or manual means (pulled by a user of device 110 or actuated via actuation module 200). The opposite end of pulley wire 160 may be affixed to the bottom front portion of flexible tip 170 (attached to the front disc 171). Once pulley wire 160 is pulled, it is wound around pulley 164 and simultaneously pulls flexible tip 170 anteriorly and inferiorly to position flexible tip 170 at the laryngeal opening 213 of patient 105 and increases the likelihood of successful insertion of ETT 130 into the laryngeal opening 213. It is noted that flexible tip 170 is able to be pulled anteriorly and inferiorly (as shown) due to the top of pulley 164 being positioned above the bottom of flexible tip 170 (where pulley wire 160 is affixed).

Positioning of the flexible tip 170 may occur once the expansion of hood body 212 is separately carried out to clear the soft tissue from the hypopharyngeal and laryngeal vestibule. Additionally, flexible tip 170 may be pulled farther (along with overtube 120) by alternative tip director 165 in response to locking mechanism 190 being unlocked/in an unlocked position or state and in response to the expansion of hood body 212.

In embodiments, locking mechanism 190 may be controlled via user input entered into control unit 270. User input for unlocking locking mechanism 190 may include the use of screens, buttons, switches, controls etc. Control unit 270 may receive the user input as gestures such as, but not limited to touch screen gestures and button/switch/control actuating. In other embodiments, locking mechanism 190 may comprise multiple configurations besides the protrusion-groove mechanism that may be easily conceived of by one skilled in the art. Other configurations may include, but are not limited to male-female engagement mechanisms, twist-lock mechanisms, threaded bearing mechanisms, and magnetic mechanisms. It is noted that in the case where locking mechanism 190 is controlled by user input, locking mechanism 190 may be unlocked prior to hood body 212 being inflated since the unlocking is not dependent on the expansion of hood body 212 in this case.

In embodiments, inflatable bladder 212 affixed to the free edge of hood base 211 (side walls of hood base 211) via one or more attachment means such as, but not limited to, adhesive, heat bonding, solvent bonding, and ultrasonic welding.

FIG. 8 displays a components diagram of an intubation device 110 in accordance with embodiments. Actuation module 200 may house one or more motors 250 affixed to one or more gears 255. The motors 250 and gears 255 in actuation module 200 may be utilized to move the flexible tip 170 using wires 172 as well as to actuate first chain 188 and second chain 198 to rotate first roller 181 of feeder mechanism 180 and to pull second roller 191 adjacent ETT 130. Power source 257 may be electrically connected to video monitor 140, camera 168, and light source 167 in order to provide power and have the video monitor 140, camera 168, and light source 167 function. Pump device 260 may be affixed to hood 210 via inflation tube 214 and may provide air to inflatable bladder for inflation. Pump device 260 may comprise devices such as, but not limited to, a hand pump, electric pump, a free syringe, etc. Control unit 270 may be electrically connected to power source 257 and at least one of actuation module 200, feeder mechanism 180, video monitor 140, pump device 260, camera 168, and light source 167. Control unit 270 may receive user input that may be translated into functions for the mentioned elements;

these functions may include, but are not limited to: up, down, left, right, inflate, deflate, on, off, power up (scaled), power down (scaled), fast (scaled), and slow (scaled). In embodiments, user input may be input into control unit 270 via at least one of buttons and dials. Power source 257 may be electrically connected to at least one of control unit 270, actuation module 200, feeder mechanism 180, video monitor 140, pump device 260, camera 168, and light source 167 in order to provide electricity to these components. It is noted that FIG. 8 displays one or more embodiments of an intubation device 110; these embodiments may include one or more elements of this disclosure that are not found in FIG. 8.

Figure 9A:
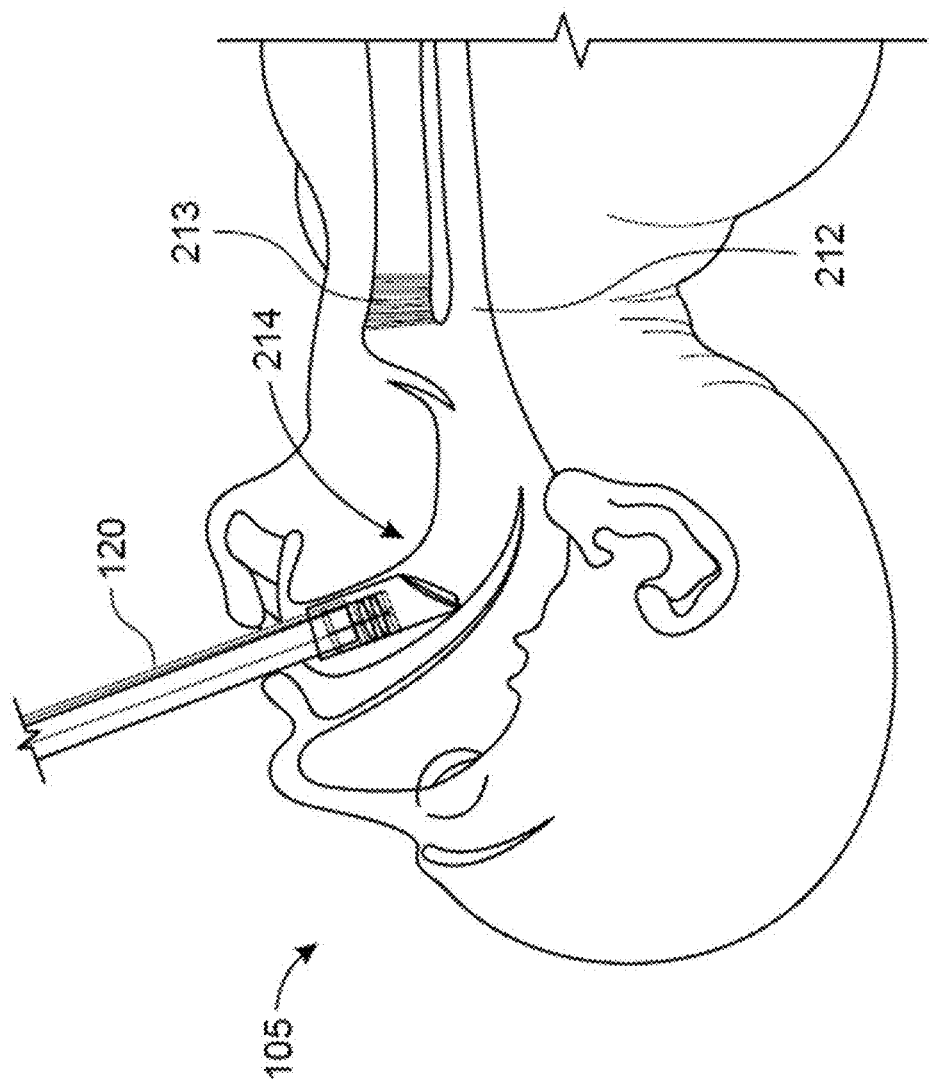
FIG. 9A displays an internal view of a laryngoscopy device partially inserted into a patient's throat in accordance with embodiments.
Figure 9B:
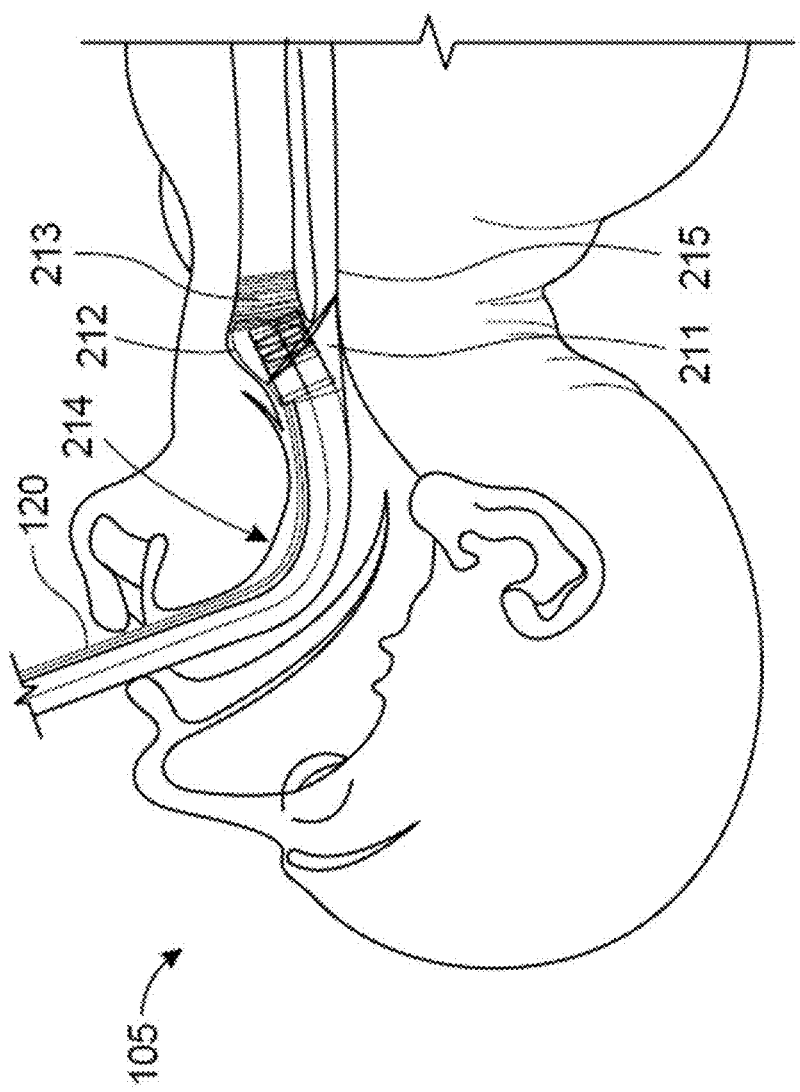
FIG. 9B displays an internal view of an intubation device fully inserted into a patient's throat in accordance with embodiments.

FIG. 9A displays an internal view of an intubation device 110 partially inserted into a patient's throat 214 in accordance with embodiments. When a patient 105 is not breathing and needs an ETT 130 inserted into their laryngeal opening 213, a distal end 121 of overtube 120 and flexible tip 170 may be inserted into the throat 214 of a patient 105. When in a proper position, hood base 211 may sit against the posterior hypopharyngeal wall with the esophageal seal occluding the esophageal inlet 215. As shown in FIG. 9B, hood body 212 may then be inflated, thus becoming rigid and is able to push out the soft tissue from the hypopharynx and laryngeal vestibule 213 in throat 214.

Figure 9C:
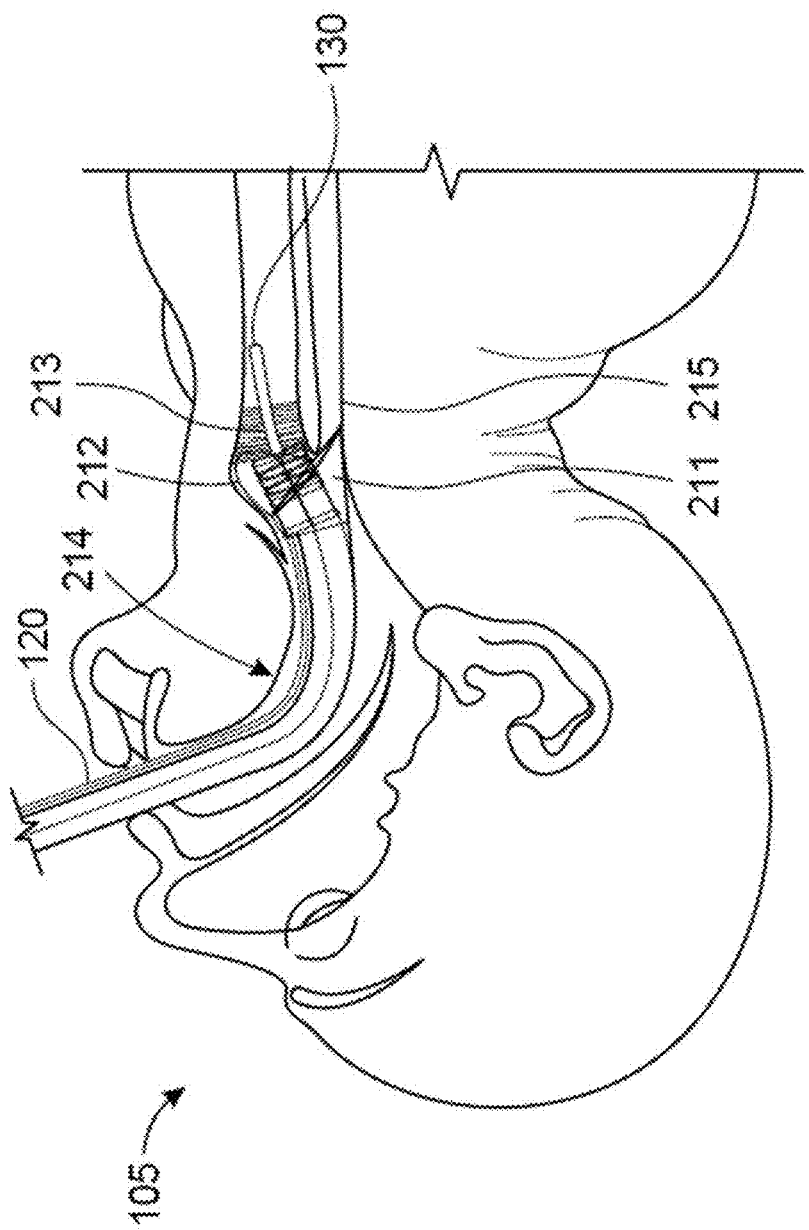
FIG. 9C displays an internal view of an intubation device fully inserted into a patient's throat with an intubation tube positioned in a larynx in accordance with embodiments.

When hood body 212 is expanded, flexible tip 170 may be automatically pulled anteriorly and inferiorly via tip director 169/alternative tip director 165 and may position flexible tip 170 (and ETT 130 positioned within flexible tip 170) at the laryngeal opening 213 of patient 105 and increases the likelihood of successful insertion of ETT 130 into the laryngeal opening 213 (see FIG. 9C). Additionally, when expanded, hood body 212 may expand outwardly away from base 211 to push out the soft tissue from the hypopharynx and laryngeal vestibule 213 in the throat 214, clearing the visual pathway. In this position, hood body 212/inflatable bladder may provide an airtight seal so that the oxygen from ventilator 103 is directed into patient 105 rather than escaping out of the patient 105.

Camera 168 and light source 167 may be utilized to see if the ETT 130 is in a position to be fed into the laryngeal opening 213. If the ETT 130 is not optimally positioned, actuation module 200 may be utilized to adjust the lengths of wires 172 to move flexible tip 170, and thus ETT 130, into an optimal position to be fed into laryngeal opening 213.

Figure 10A:
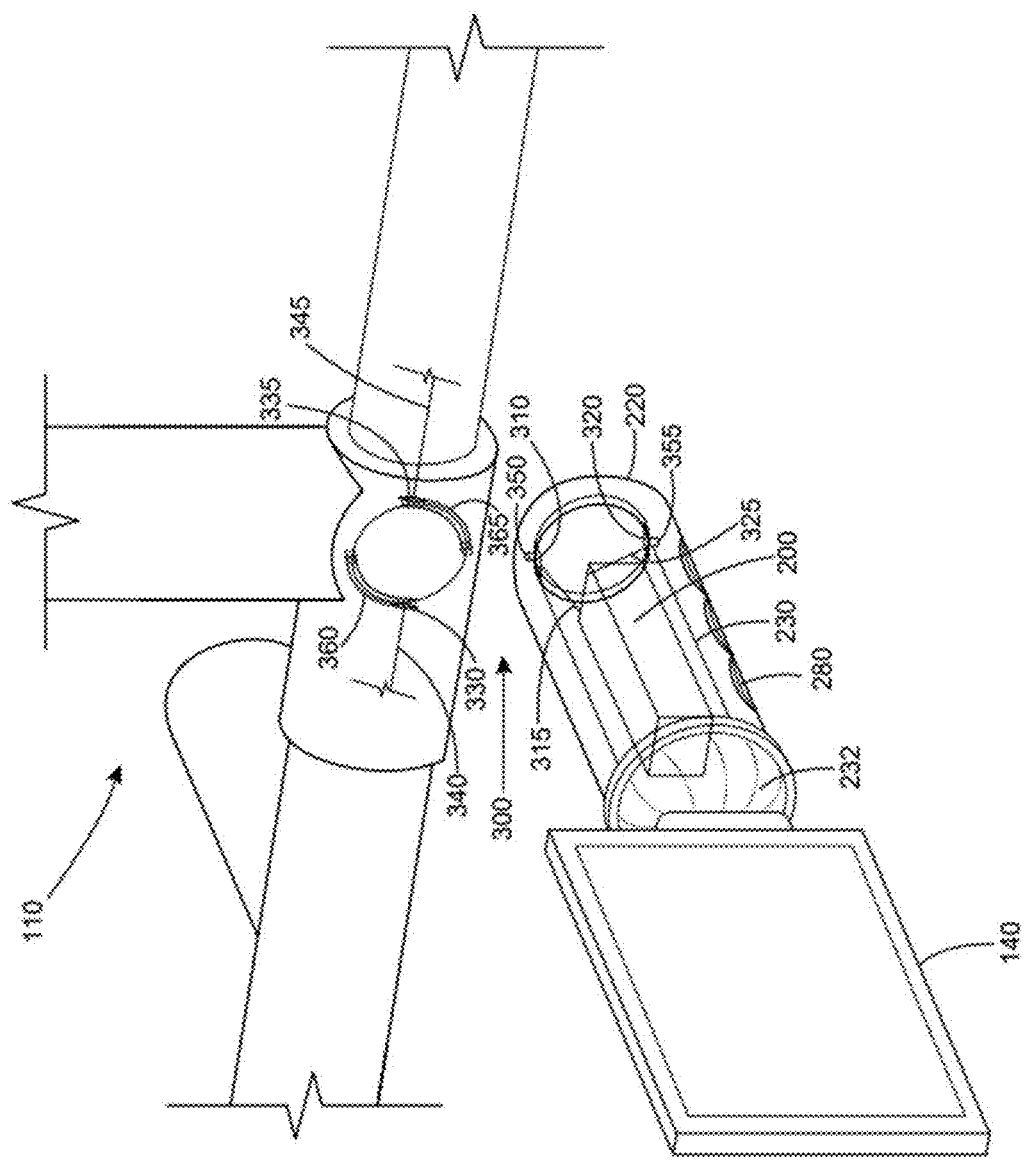
FIG. 10A displays a perspective view of a snap-twist locking mechanism in accordance with embodiments.

FIG. 10A displays a perspective view of a snap-twist locking mechanism 300 in accordance with embodiments. Handle 220 is shown detached from the rest of device 110. In this embodiment, handle 220 may be removably affixable to the rest of device 110 via a twist-locking mechanism 300 as shown. Twist-locking mechanism 300 may include first passage 360 and second passage 365 positioned internally inside of device 110. First and second passages 360,365 may each extend roughly 90 degrees in order to provide a passage for a first and second protrusion 350,355 to a first and second conductive receiver 330,335. Handle 220 may include first protrusion 350 and second protrusion 355 which are affixed to first and second wire terminals 310,320, respectively. First and second wire terminals 310,320 may be positioned on an interior wall of handle 220 and may be affixed to first wire 315 and second wire 325, respectively. First and second wire 315,325 may also be affixed to power source 257 housed in actuation module 200 (positioned within interior section 230 of handle 220) in order to supply electricity through the circuit that is created when handle 220 is properly affixed to the rest of device 110. In embodiments, handle 220 may also include control unit 270 (not depicted) that may also be positioned within interior section 230. On the distal end of handle 220 (opposite locking mechanism 300), video monitor 140 may be affixed to handle 220 via monitor retainer 232. In embodiments, video monitor 140 may be removably affixable to monitor retainer 232 via means such as, but not limited to threading, twist-lock engagement, O-ring attachment, magnetic attachment, form-fitting, and male-female engagement. In other embodiments, monitor retainer 232 may be removably affixable to handle 220 via means such as, but not limited to threading, twist-lock engagement, O-ring attachment, magnetic attachment, form-fitting, and male-female engagement; monitor retainer 232 may then be affixed to another portion of device 110.

Figure 10B:
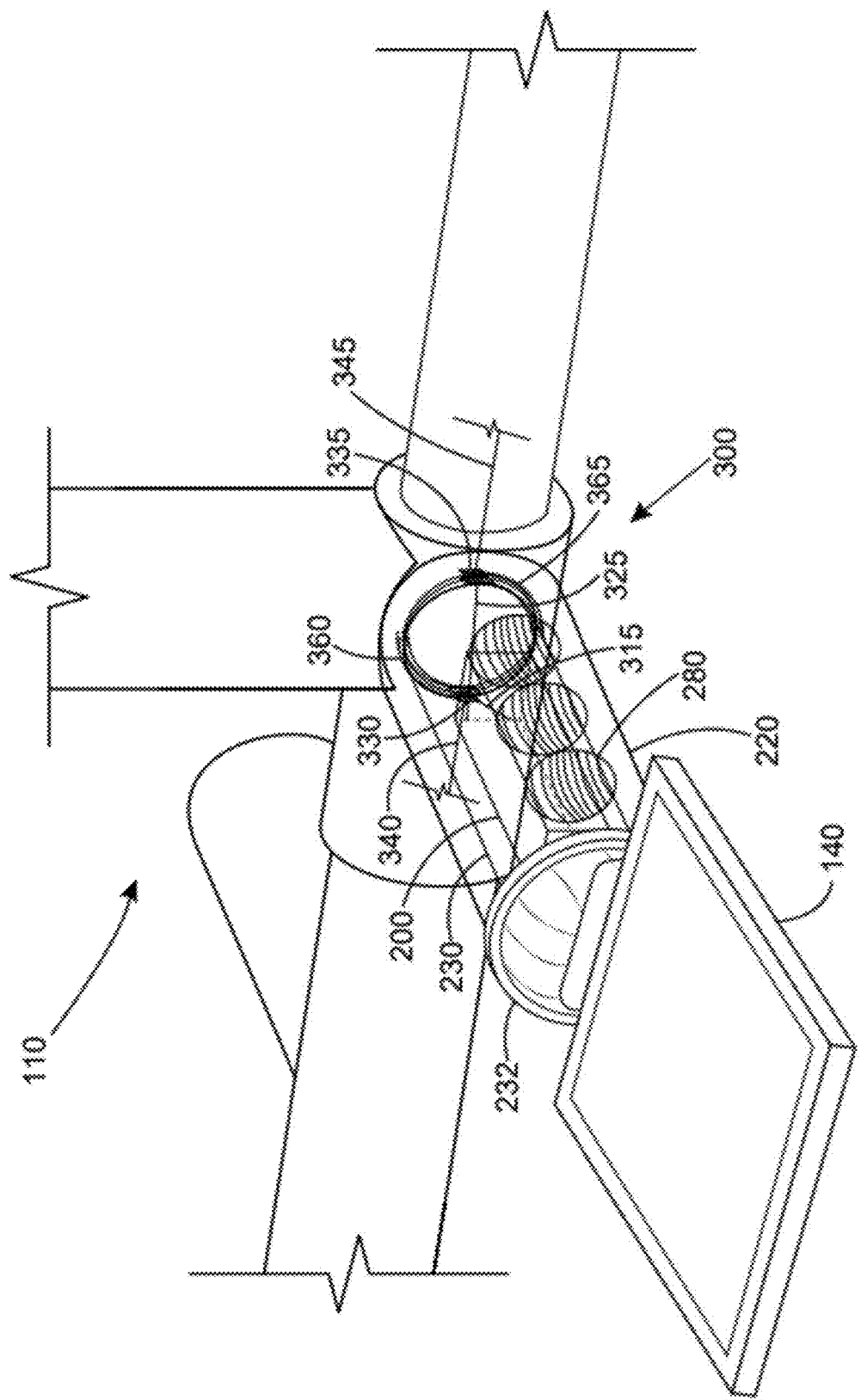
FIG. 10B displays a perspective view of a snap-twist locking mechanism completing a circuit in accordance with embodiments.

In order to close the circuit, first and second protrusions 350,355 of handle 220 are inserted into first and second passages 360,365. Once inserted, handle 220 is turned counterclockwise 90 degrees until first and second protrusions 350,355 contact first and second conductive receivers 330,335, as shown in FIG. 10B. First and second conductive receivers 330,335 may comprise a configuration for securely receiving first and second protrusions 350,355 such as, but not limited to an orifice and an indented shape. When this positioning is accomplished, the circuit between the handle 220 and the device 110 becomes closed and one or more motors (motor 250 or otherwise) contained in device 110 (in handle 220/actuation module 200 or in another part of device 110) may provide power to one or more of the aforementioned electric powered elements of device 110 (pending the use of any control switches) via third wire 340 and fourth wire 345 positioned in device 110. It is noted that when the circuit is closed, electricity is sent from power source 257 to one or more motors (motor 250 or otherwise) that may be positioned anywhere along/within device 110 and connected via third and fourth wires 340,345. In order to keep the handle 220 contained within device 110, handle 220 may be secured using a male-female engagement mechanism with device 110 such as the mechanisms mentioned previously. In certain embodiments, first and second protrusions 350,355 may be spring-loaded in order for handle 220 to be more easily inserted into and/or removed from device 110.

In embodiments, the spring-loaded mechanism of first and second protrusions 350,355 may be controlled using trigger mechanism 280. It is noted that one skilled in the art can conceive of and create the components for using trigger mechanism 280 as an actuator for the spring-loaded mechanism of first and second protrusions 350,355. In other embodiments, trigger mechanism 280 may be used as a switch for the circuit of device 110. It is noted that one skilled in the art can conceive of and create the components for using trigger mechanism 280 as a switch for the circuit of device 110.

When handle 220 comprises actuation module 200 and/or power source 257, it is noted that handle 220 (and any components it contains) may be kept in a medical setting as a standard piece of equipment, while the rest of device 110 may be disposable (as a single-use product or a product that is only used a few times). In this embodiment, handle 220 may also include control unit 270.

Figure 11:
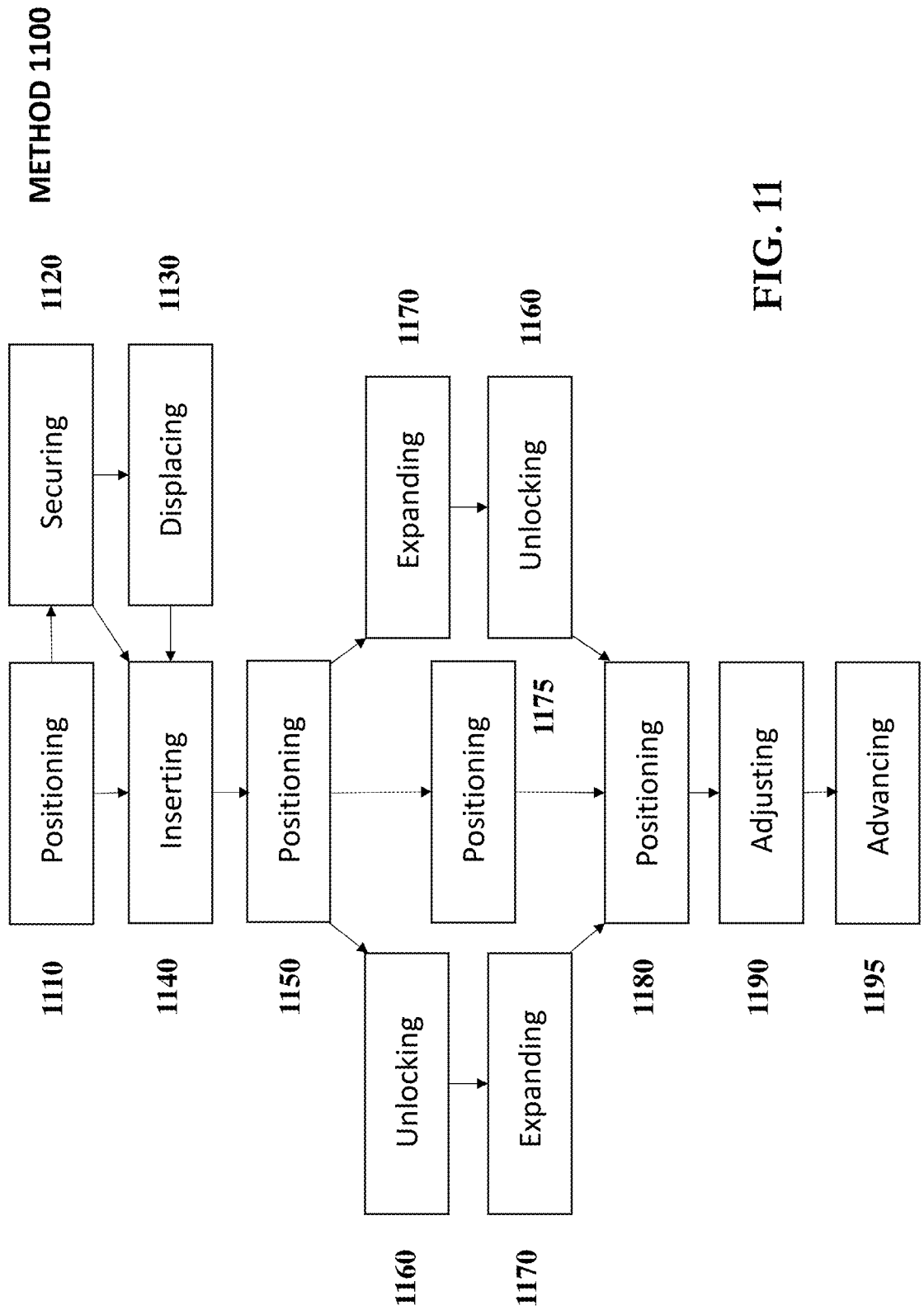
FIG. 11 displays a method for inserting an ETT into a patient's trachea in accordance with embodiments.
Figure 12:
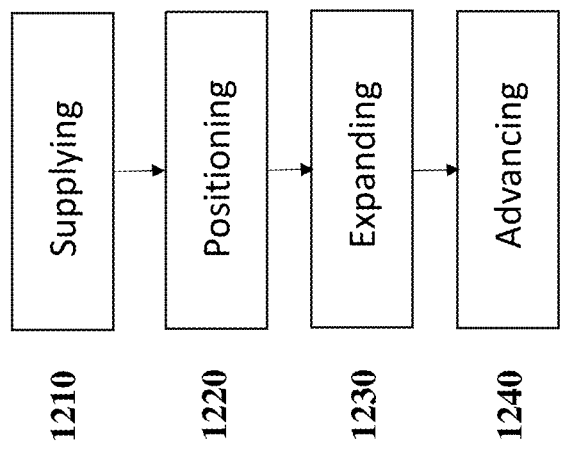
FIG. 12 displays a method for clearing soft tissue from a larynx and hypopharynx of a patient in accordance with embodiments.

FIG. 11 displays a method 1100 for inserting an ETT 130 into the trachea of a patient 105 in accordance with embodiments. Method 1100 may comprise positioning 1110 an ETT 130 within an overtube 120. This may be carried out by inserting ETT 130 through either the proximal opening (actuation module orifice 123) or distal opening 124 (opening in hood 210) of the overtube 120 until the ETT 130 is completely inside overtube 120. Device 110 may then be inserted 1140 into a patient's throat 214. Once the device 110 is in the throat 214 of patient 105, device 110 may be moved down the throat 214 until flexible tip 170 of device 110 is positioned 1150 adjacent a patient's laryngeal opening 213. Locking mechanism 190 between hood 210 and overtube 120 may then be unlocked 1160, allowing overtube 120 to slide/advance within hood 210 (the unlocking 1160 may be carried out via user input entered into control unit 270). Hood body 212 is then expanded 1170 (via means previously discussed such as, in embodiments, via inflation tube 216). Since the anteroinferior portion of hood body 212 and the distal end 121 of overtube 120 are connected via tip director 169, hood body 212 pulls overtube 120 anteroinferiorly. The end result of this expanding 1170 motion is the positioning 1180 of flexible tip 170 at the laryngeal opening 213. In another embodiment, alternative tip director 165 is utilized to position 1175 the overtube adjacent the laryngeal opening 213. Thusly positioned overtube 120 may optionally be further adjusted 1190 via articulating function of the flexible portion of overtube 120 (extension and retraction of the plurality of wires 172). ETT 130 may then be advanced 1195 into the trachea through a plurality of means, such as, but not limited to any of the aforementioned feeder mechanisms 180.

In embodiments, method 1100 may include securing 1120 ETT 130 within the overtube 120 via a feeder mechanism 180 positioned within overtube 120 after the positioning 1110. The securing 1120 may further include laterally displacing 1130 a first roller 181 of the feeder mechanism 180 towards a second roller 191 of feeder mechanism 180 so that ETT 130 is secured within overtube 120.

In embodiments, method 1100 may comprise providing air to an end of the overtube 120 adjacent the laryngeal opening 213 via a ventilator 103. The providing of air may be performed after the positioning 1150 of flexible tip 170 and may be performed if hood body 212 is inflatable (includes an inflatable bladder).

In other embodiments of method 1100, the unlocking 1160 may be dependent upon the inflating 1170 if a locking mechanism 190 not controlled by user input is utilized. In this case, locking mechanism 190 unlocks 1160 when tip director 169 is pulled due to the expanding 1170; expanding 1170 may therefore occur before the unlocking 1160.

FIG. 11 displays a method 1200 for clearing soft tissue from a larynx and hypopharynx of a patient 105 in accordance with embodiments. Method 1200 may utilize any of the aforementioned embodiments of device 110. Method 1200 may include supplying 1210 a device 110 having an overtube 120, an ETT 130 disposed in overtube 120, a hood 210 having an expandable hood body 212, and, in embodiments where the hood body 212 is inflatable, a pump device 260 and an inflation tube 216 connecting an inflatable bladder of hood body 212 and pump device 260. Device 110 may then be positioned 1220 in a throat 214 of a patient 105 adjacent the laryngeal opening 213. Hood body 212 may then be expanded 1230 (via means previously discussed such as, in embodiments, via inflation tube 216) and may become rigid and expand in a centrifugal manner in an environment adjacent the laryngeal opening 213. As the expansion 1230 occurs, the soft tissue of the larynx and hypopharynx may be pushed away from the line of vision of device 110, allowing space for advancement 1240 of ETT 130 into the trachea. Advancement 1240 of ETT 130 may occur through a plurality of means, such as, but not limited to any of the aforementioned feeder mechanisms 180.

It is noted that certain elements are not drawn to scale and it would be obvious to one skilled in the art how to amend the elements to be properly scaled in relation to other elements.

It is noted that the utilization of handle 220 adds increased stability to the removal process of removing device 110 from a patient's throat 214.

In any of the aforementioned embodiments, any wiring or wires 172 may be embedded within the thickness/wall of overtube 120 instead of being covered by flexible sheath 176.

In any of the aforementioned embodiments, gears 187, 197,255 may not include cogs and may comprise a pulley structure. In other embodiments, the pully structure may include cogs in the grooved portion of the pulley structure. Additionally, in other embodiments, chains 188,198 may instead comprise a wire-like structure. In other embodiments, the wire-like structure may include protrusions (similar to cogs) that may fit properly into any cogs on gears 187,197,255 and/or pulley structure.

For the purposes of this disclosure, the terms "hood 210" and "hood portion 210" may be synonymous.

For the purposes of this disclosure, the terms "ETT 130" and "endotracheal tube 130" may be synonymous.

For the purposes of this disclosure, the terms "wire 172" and "control wire 172" may be synonymous.

For the purposes of this disclosure, the terms "malleable covering 175" and "covering 175" may be synonymous.

For the purposes of this disclosure, the terms "inflatable bladder" and "bladder" may be synonymous.

For the purposes of this disclosure, the terms "laryngeal opening 213" and "laryngeal vestibule 213" may be synonymous.

Unless otherwise defined, all technical and scientific terms used herein have the same meanings as are commonly understood by one of ordinary skill in the art to which this disclosure belongs. Although methods similar or equivalent to those described herein can be used in the practice or testing of the present disclosure, suitable methods are described herein.

All publications, patent applications, patents, and other references mentioned herein are incorporated by reference in their entirety. In case of conflict, the patent specification, including definitions, will prevail. In addition, the materials, methods, and examples are illustrative only and not intended to be limiting.

It will be appreciated by persons skilled in the art that the present disclosure is not limited to what has been particularly shown and described hereinabove. Rather, the scope of the present disclosure is defined by the appended claims and includes both combinations and sub-combinations of the various features described hereinabove as well as variations and modifications thereof, which would occur to persons skilled in the art upon reading the foregoing description.

The invention claimed is:

1. An intubation device comprising:
   an overtube having:
      a semirigid portion having a proximal end and a distal end; and
      a flexible tip affixed at the distal end; and
      a lumen configured to accommodate an ETT;
   a feeder mechanism for advancing the ETT through the overtube;
   and
   a hood affixed to the distal end of the overtube, the hood comprising;

a base contiguous with a posterior wall of a hood stem; and a body having an expandable structure, wherein the body spans the width of an opening of the hood; a tip director affixed to the hood body and the overtube, the tip director configured to advance the overtube toward a laryngeal opening when the hood body is expanded.

2. The device of claim 1, wherein the feeder mechanism for the ETT comprises at least one of manual functionality and automatic functionality.

3. The device of claim 1, the tip director further comprises:

a wire affixed to the overtube and an actuation module; and a pulley affixed to the hood base, wherein the actuation module is configured to retract the wire around the pulley in order to advance the overtube toward a laryngeal opening.

4. The device of claim 1, wherein the hood stem is positioned over the distal end of the overtube.

5. The device of claim 1, further comprising a plurality of wires affixed to an actuation module and the flexible tip, wherein the actuation module extends and retracts the plurality of wires to articulate the flexible tip.

6. The device of claim 1, wherein further comprising a handle removably affixable to the intubation device.

7. The device of claim 1, wherein the hood body comprises a distal edge having an arc shape and spanning from a first sidewall of the hood base to a second sidewall of the hood base when the hood body is expanded, further wherein lateral edges of the hood body are affixed along the first sidewall and the second sidewall of the hood base.

8. The device of claim 1, wherein the hood opening comprises an oblique, ellipsoid shape.

9. The device of claim 1, wherein the hood body is outwardly extensible from the base to provide an airtight seal at the location adjacent the laryngeal opening.

10. The device of claim 1, wherein the overtube is affixable to a ventilator to provide air to the location adjacent the laryngeal opening during an intubation process.

11. The device of claim 1, further comprising a video monitor system including a video monitor and a camera affixed to an interior surface of the flexible tip.

12. A method for inserting and positioning an ETT into a trachea of a patient, comprising:

positioning an ETT within an overtube;

inserting the overtube into the throat of the patient, the overtube including a flexible tip positioned at a distal end of the overtube;

articulating the flexible tip to adjust the positioning of the overtube at a laryngeal opening of the patient;

expanding a hood body of a hood, the hood positioned at the distal end of the overtube, the hood body spanning the width of an opening of the hood, wherein the expanding makes the expandable hood body rigid and moves the hood body outwardly away from the hood opening; and advancing the ETT through the hood opening and the layngeal opening into the trachea of the patient; wherein the advancing is accomplished via at least one of: manual advancement and actuation of a feeder mechanism; a tip director affixed to the hood body and the overtube, the tip director configured to advance the overtube toward a laryngeal opening when the hood body is expanded.

13. The method of claim 12, further comprising securing the ETT within the overtube via the feeder mechanism.

14. The method of claim 12, further comprising advancing the overtube within the hood via dislodging of at least one protrusion of a hood sleeve, each of the at least one protrusion lodged in a respective pocket of the overtube prior to the dislodging.

15. The method of claim 12, wherein the hood body comprises a distal edge having an arc shape and spanning from a first sidewall of the hood base to a second sidewall of the hood base when the hood body is expanded, further wherein lateral edges of the hood body are affixed along the first sidewall and the second sidewall of the hood base.

16. The method of claim 12, wherein the articulating of the flexible tip occurs in response to extension and retraction of a plurality of wires via an actuation module.

17. The method of claim 12, further comprising providing air to an end of the overtube adjacent the laryngeal opening via a ventilator.

18. The method of claim 12, further comprising advancing the overtube adjacent the laryngeal opening by actuating the tip director.

19. A method for clearing soft tissue from a larynx and hypopharynx of a patient, comprising:

supplying a device comprising:
an overtube;
an ETT disposed in the overtube; and
a hood having an expandable hood body, the hood body spanning the width of an opening of the hood;

positioning the device in a throat of a patient;

advancing the overtube adjacent the laryngeal opening by actuating a tip director; and expanding the expandable hood body in order to make the expandable hood body rigid, wherein the expanding moves the expandable hood body outwardly and away from the hood opening;

wherein the expanding pushes soft tissue away from an opening of the hood; a tip director affixed to the hood body and the overtube, the tip director configured to advance the overtube toward the laryngeal opening when the hood body is expanded.

* * * * *